United States Patent
Bolund et al.

(10) Patent No.: US 10,729,112 B2
(45) Date of Patent: Aug. 4, 2020

(54) PIG MODEL FOR DIABETES

(71) Applicant: Aarhus Universitet, Aarhus C (DK)

(72) Inventors: Lars Bolund, Skødstrup (DK); Yonglun Luo, Egå (DK)

(73) Assignee: Aarhus Universitet, Aarhus C (DK)

( * ) Notice: Subject to any disclaimer, the term of this patent is extended or adjusted under 35 U.S.C. 154(b) by 0 days.

(21) Appl. No.: 15/506,388

(22) PCT Filed: Aug. 28, 2015

(86) PCT No.: PCT/DK2015/050253
§ 371 (c)(1),
(2) Date: Feb. 24, 2017

(87) PCT Pub. No.: WO2016/029919
PCT Pub. Date: Mar. 3, 2016

(65) Prior Publication Data
US 2017/0231204 A1    Aug. 17, 2017

(30) Foreign Application Priority Data
Aug. 28, 2014 (DK) .......................... PA 2014 70518

(51) Int. Cl.
| | |
|---|---|
| *A01K 67/027* | (2006.01) |
| *C12N 15/877* | (2010.01) |
| *C07K 14/47* | (2006.01) |
| *C12N 15/90* | (2006.01) |
| *G01N 33/66* | (2006.01) |
| *G01N 33/68* | (2006.01) |
| *G01N 33/74* | (2006.01) |

(52) U.S. Cl.
CPC .......... *A01K 67/0278* (2013.01); *C07K 14/47* (2013.01); *C07K 14/4711* (2013.01); *C12N 15/8778* (2013.01); *C12N 15/907* (2013.01); *G01N 33/66* (2013.01); *G01N 33/68* (2013.01); *G01N 33/74* (2013.01); *A01K 2207/15* (2013.01); *A01K 2217/072* (2013.01); *A01K 2227/108* (2013.01); *A01K 2267/0362* (2013.01)

(58) Field of Classification Search
CPC .......................... A61K 67/0278; C12N 15/907
See application file for complete search history.

(56) References Cited

U.S. PATENT DOCUMENTS

2009/0271882 A1    10/2009 Umeyama

FOREIGN PATENT DOCUMENTS

| EP | 2077330 A | 7/2009 |
|---|---|---|
| WO | 9637612 A1 | 11/1996 |
| WO | 2005015990 A1 | 2/2005 |
| WO | 2013192316 A1 | 12/2013 |
| WO | 2014117045 A2 | 7/2014 |

OTHER PUBLICATIONS

Naito et al. J Reprod Fert 113:137-143, 1998. (Year: 1998).*
Raina et al. Gene 96-100, 2015. (Year: 2015).*
Dolatshad et al. Mammalian Genome 26:598-608, 2015 (Year: 2015).*
Yao et al. Scientific Reports 4:6926. DOI:10.1038/srep06926. Nov. 2014. pp. 1-8 (Year: 2014).*
Laible et al. Biotechnology Journal 10:109-120, 2015 (Year: 2015).*
Gao et al. Genome Biology 18:1-15, 2017 (Year: 2017).*
Search results from "reflected definition" in Google, printed Jan. 3, 2020, p. 1-3. (Year: 2020).*
Renner, Simone et al; "Permanent Neonatal Diabetes in INSC94Y Transgenic Pigs"; Diabetes, vol. 62, May 2013.
Andersen, Marie S. et al; "Mechanisms underlying targeted gene correction using chimeric RNA/DNA-stranded DNA and single-stranded DNA oligonucleotides"; Journal of Mol. Med. 2002; 80:770-781.
Book, Steven A et al; "The fetal and neonatal pig in biomedical research"; Journal of Animal Science, vol. 38, No. 5, 1974.
Butler, ; E. et al; Diabetes Due to a Progressive Defect i B-Cell Mass in Rats Transgenic for Human Islet Amyloid Polypeptide (Hip Rat); Diabetes, vol. 53; Jun. 2004; pp. 1509-1516.
Carlson, Daniel F. et al; "Efficient Talen-mediated gene knockout in livestock"; Proc. Natl. Acad. Sci. USA; Oct. 23, 2012; 109(43) 17382-7.
Couce, Martha et al; "Treatment With Growth Hormone and Dexamethasone in Mice Transgenic for Human Islet Amyloid Polypeptide Causes Islet Amyloidosis and B-Cell-Dysfunction"; Diabetes; vol. 45; Aug. 1996; 1094-1101.
Douglas, William Richard; "Of Pigs and Men and Research"; Space Life Sciences 2, 1972, pp. 226-234.
Geurtz, Aron M. et al; "Knockout Rats via Embryo Microinjection of Zinc-Finger Nucleases"; Science; vol. 325; Jul. 24, 2009.
Hiddinga, Henry J. et al; "Expression of wild-type and mutant S20G hIAPP in physiologic knock-in mouse models fails to induce islet amyloid formation, but induces mild glucose intolerance"; Journal of Diabetes Investigation, vol. 3, Apr. 2, 2012.
Hull, Rebecca L. et al; "Islet Amyloid: A Critical Entity in the Pathogenesis of Type 2 Diabetes"; Journal of Clinical Endocrinology & Metabolism; vol. 89, No. 8; Aug. 1, 2004, pp. 3629-3643.
Ivics, Zoltan et al; "Molecular Reconstruction of Sleeping Beauty; a Tc1-like Transposon from Fish, and Its Transposition in Human Cells"; Cell; vol. 91; Nov. 14, 1997; 501-510.

(Continued)

*Primary Examiner* — Marcia S Noble
(74) *Attorney, Agent, or Firm* — Dinsmore & Shohl LLP; Weston R. Gould

(57) ABSTRACT

The present invention relates to a transgenic pig comprising a mutated IAPP gene and displaying a phenotype associated with diabetes. The invention also relates to a transgenic blastocyst, embryo, fetus, donor cell and/or cell nucleus derived from said transgenic pig. The invention further relates to use of the transgenic pig as a model system for studying therapy, treatment and/or prevention of diabetes.

16 Claims, 9 Drawing Sheets

Specification includes a Sequence Listing.

(56) References Cited

OTHER PUBLICATIONS

Janson, Juliette et al; "Spontaneous diabetes mellitus in transgenic mice expressing human islet amyloid polypeptide"; Proc. Natl. Acad. Sci. USA; vol. 93, pp. 7283-7288, Jul. 1996.

Kragh, P. M. et al; "Combined electrical and chemical activation of zona-free porcine oocytes"; Reproduction, Fertility and Development; 16:290, pp. 284-285, 2004.

Liu, H. et al; "Targeted beta-globin gene conversion in human hematopoietic CD34+ and Lin-CD38–cells"; Gene Therapy (2002) 9, pp. 118-126.

Liu, Huan et al; Development of Transgenic Minipigs with Expression of Antimorphic Human Cryptochrome 1; PLOS ONE, vol. 8, Issue 10, e76098, 2013.

Matveyenko, Aleksey V. et al; "Islet Amyloid Polypeptide (IAPP) Transgenic Rodents as Models for Type 2 Diabetes"; Ilar Journal; vol. 47, No. 3; Jan. 1, 2006.

Morita, Shuhei et al; "Progressive deterioration of insulin secrection in Japanese type 2 diabetic patients in comparison with those who carry the S20G mutation of the islet amyloid polypeptide gene: A long-term follow up study"; Journal of Diabetes Investigation vol. 2, Issue 4 Aug. 2011.

O'Brien, Timonty D. et al; "Human islet Amyloid Polypeptide Expression in COS-1 Cells. A Model of Intracellular Amyloidogenesis"; American Journal of Pathology; vol. 147, No. 3; Sep. 1, 1995.

Renner, Simone et al; "Glucose Intolerance and Reduced Proliferation of Pancreatic b-Cells in Transgenic Pigs with Impaired Glucose-Dependent Insulinotropic Polypeptide Function"; Diabetes, vol. 59, May 2010.

Sørensen, Charlotte B. et al; "Site-specific strand bias in gene correction using single-stranded oligonucleotides"; Journal of Mol. Med. (2005) 83:39-49.

Umeyama, Kazuhiro et al; "Dominant-negative mutant hepatocyte nuclear factor 1x induces diabetes in transgenic-cloned pigs"; Transgenic , Apr. 9, 2009; pp. 697-706.

Urnov, Fyodor D. et al; Highly efficient endogenous human gene correction using designed zinc-finger nucleases; Nature; vol. 435; Jun. 2, 2005.

Vajta, G. et al; "New Method for Culture of Zona-Included or Zona-Free Embryos: The Well of the Well (WOW) System"; Molecular Reproduction and Development 55:256-264; 2000.

Westermark, Per er al; "Islet amyloid polypeptide: Pinpointing amino acid residues linked to amyloid fibril formation"; Proc. Natl, Acad. Sci. USA; vol. 87, pp. 5036-5040; Jul. 1990.

Wolf, E. et al; "Genetically engineered pig models for diabetes research"; Transgenic Res., 2014; 23:27-38.

Yoshioka, Koji et al; "Birth of Piglets Derived from Porcine Zygotes Cultured in a Chemically Defined Medium"; Biology of Reproduction 66, 112-119, 2002.

Zhang, Xin et al; "Porcine islet amyloid polypeptide fragments are refractory to amyloid formation". FEBS Letters 585(1); 2011; pp. 71-77.

* cited by examiner a

| Transfer ID | Nr. of embryos | Pregnant | Abortion | Litter Size | Piglet ID* |
|---|---|---|---|---|---|
| 2477 | 75 | Yes | No | 3 | S1, S2, HIP609 |
| 2532 | 75 | Yes | Yes | NA | NA |
| 2533 | 83 | Yes | No | 2 | S3, HIP610 | b

HIP609    HIP610 c d

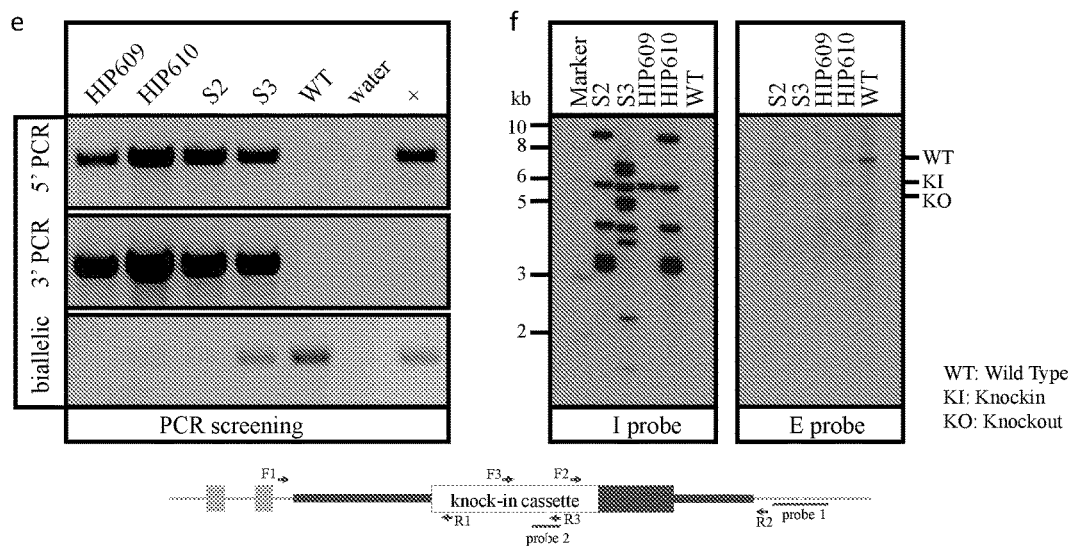
Fig. 3, continued

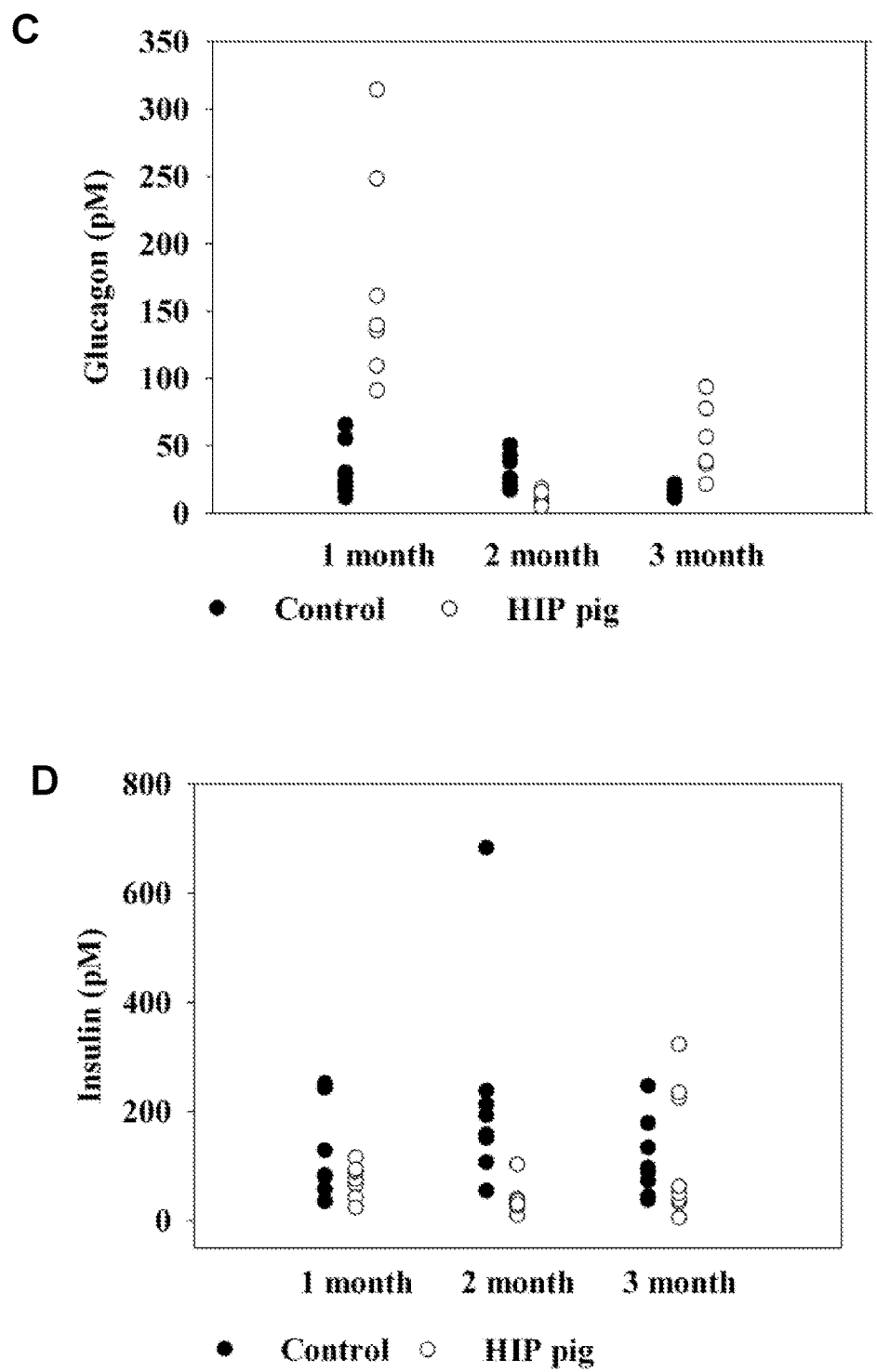
Fig. 5, continued

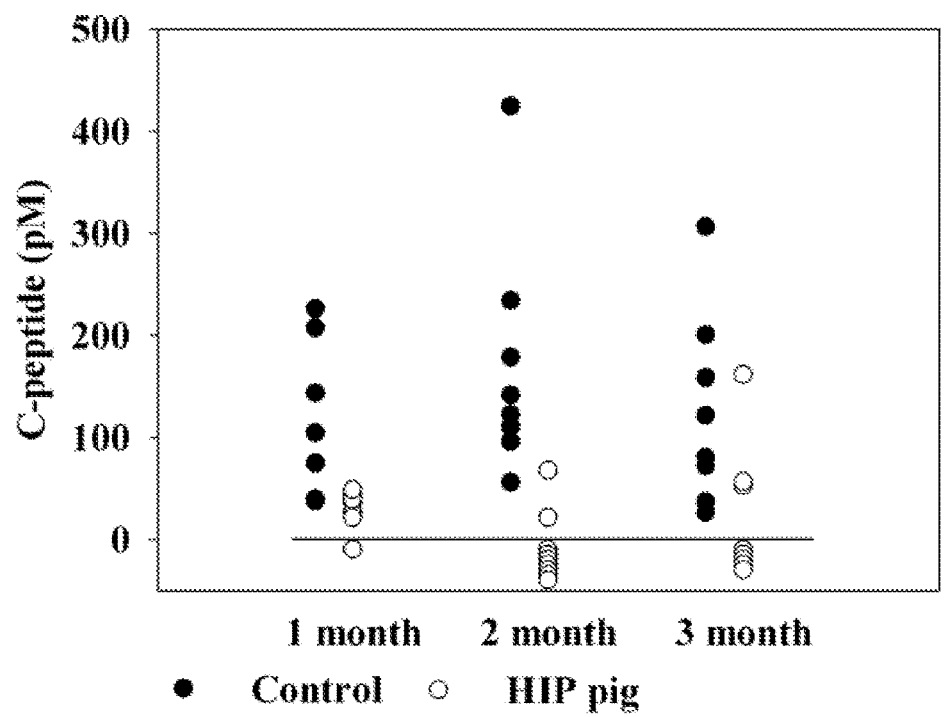
Fig. 5, continued

SEQUENCE LISTING

<160> NUMBER OF SEQ ID NOS: 17

<210> SEQ ID NO 1
<211> LENGTH: 270
<212> TYPE: DNA
<213> ORGANISM: Homo sapiens

<400> SEQUENCE: 1
atgggcatcc tgaagctgca agtatttctc attgtgctct ctgttgcatt gaaccatctg      60
aaagctacac ccattgaaag tcatcaggtg aaaagcgga aatgcaacac tgccacatgt      120
gcaacgcagc gcctggcaaa ttttttagtt cattccagca acaactttgg tgccattctc      180
tcatctacca acgtgggatc caatacatat ggcaagagga atgcagtaga ggttttaaag      240
agagagccac tgaattactt gccccttag                                         270

<210> SEQ ID NO 2
<211> LENGTH: 204
<212> TYPE: DNA
<213> ORGANISM: Homo sapiens

<400> SEQUENCE: 2
acacccattg aaagtcatca ggtggaaaag cggaaatgca cactgccac atgtgcaacg      60 cagcgcctgg caaatttttt agttcattcc agcaacaact tggtgccat tctctcatct     120 accaacgtgg gatccaatac atatggcaag aggaatgcag tagaggtttt aaagagagag     180
ccactgaatt acttgcccct ttag                                             204

<210> SEQ ID NO 3
<211> LENGTH: 111
<212> TYPE: DNA
<213> ORGANISM: Homo sapiens

<400> SEQUENCE: 3
aaatgcaaca ctgccacatg tgcaacgcag cgcctggcaa attttttagt tcattccagc      60
aacaactttg gtgccattct ctcatctacc aacgtgggat ccaatacata t               111

<210> SEQ ID NO 4
<211> LENGTH: 270
<212> TYPE: DNA
<213> ORGANISM: Homo sapiens

<400> SEQUENCE: 4
atgggcatcc tgaagctgca agtatttctc attgtgctct ctgttgcatt gaaccatctg      60
aaagctacac ccattgaaag tcatcaggtg aaaagcgga aatgcaacac tgccacatgt      120
gcaacgcagc gcctggcaaa ttttttagtt cattccggca acaactttgg tgccattctc      180
tcatctacca acgtgggatc caatacatat ggcaagagga atgcagtaga ggttttaaag      240
agagagccac tgaattactt gccccttag                                         270

<210> SEQ ID NO 5
<211> LENGTH: 204
<212> TYPE: DNA

<213> ORGANISM: Homo sapiens

<400> SEQUENCE: 5

```
acacccattg aaagtcatca ggtggaaaag cggaaatgca acactgccac atgtgcaacg    60
cagcgcctgg caattttttt agttcattcc ggcaacaact ttggtgccat tctctcatct   120
accaacgtgg gatccaatac atatggcaag aggaatgcag tagaggtttt aaagagagag   180
ccactgaatt acttgcccct ttag                                          204
```

<210> SEQ ID NO 6
<211> LENGTH: 111
<212> TYPE: DNA
<213> ORGANISM: Homo sapiens

<400> SEQUENCE: 6

```
aaatgcaaca ctgccacatg tgcaacgcag cgcctggcaa attttttagt tcattccggc    60
aacaactttg gtgccattct ctcatctacc aacgtgggat ccaatacata t            111
```

<210> SEQ ID NO 7
<211> LENGTH: 87
<212> TYPE: PRT
<213> ORGANISM: Homo sapiens

<400> SEQUENCE: 7

Ile Leu Lys Leu Gln Val Phe Leu Ile Val Leu Ser Val Ala Leu Asn
1               5                   10                  15

His Leu Lys Ala Thr Pro Ile Glu Ser His Gln Val Glu Lys Arg Lys
            20                  25                  30

Cys Asn Thr Ala Thr Cys Ala Thr Gln Arg Leu Ala Asn Phe Leu Val
        35                  40                  45

His Ser Ser Asn Asn Phe Gly Ala Ile Leu Ser Ser Thr Asn Val Gly
    50                  55                  60

Ser Asn Thr Tyr Gly Lys Arg Asn Ala Val Glu Val Leu Lys Arg Glu
65                  70                  75                  80

Pro Leu Asn Tyr Leu Pro Leu
                85

<210> SEQ ID NO 8
<211> LENGTH: 66
<212> TYPE: PRT
<213> ORGANISM: Homo sapiens

<400> SEQUENCE: 8

Pro Ile Glu Ser His Gln Val Glu Lys Arg Lys Cys Asn Thr Ala Thr
1               5                   10                  15

Cys Ala Thr Gln Arg Leu Ala Asn Phe Leu Val His Ser Ser Asn Asn
            20                  25                  30

Phe Gly Ala Ile Leu Ser Ser Thr Asn Val Gly Ser Asn Thr Tyr Gly
        35                  40                  45

Lys Arg Asn Ala Val Glu Val Leu Lys Arg Glu Pro Leu Asn Tyr Leu
    50                  55                  60

Pro Leu
65

<210> SEQ ID NO 9
<211> LENGTH: 37
<212> TYPE: PRT
<213> ORGANISM: Homo sapiens

<400> SEQUENCE: 9

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 10
<211> LENGTH: 88
<212> TYPE: PRT
<213> ORGANISM: Homo sapiens

<400> SEQUENCE: 10

Gly Ile Leu Lys Leu Gln Val Phe Leu Ile Val Leu Ser Val Ala Leu
1               5                   10                  15

Asn His Leu Lys Ala Thr Pro Ile Glu Ser His Gln Val Glu Lys Arg
            20                  25                  30

Lys Cys Asn Thr Ala Thr Cys Ala Thr Gln Arg Leu Ala Asn Phe Leu
        35                  40                  45

Val His Ser Gly Asn Asn Phe Gly Ala Ile Leu Ser Ser Thr Asn Val
    50                  55                  60

Gly Ser Asn Thr Tyr Gly Lys Arg Asn Ala Val Glu Val Leu Lys Arg
65                  70                  75                  80

Glu Pro Leu Asn Tyr Leu Pro Leu
                85

<210> SEQ ID NO 11
<211> LENGTH: 66
<212> TYPE: PRT
<213> ORGANISM: Homo sapiens

<400> SEQUENCE: 11

Pro Ile Glu Ser His Gln Val Glu Lys Arg Lys Cys Asn Thr Ala Thr
1               5                   10                  15

Cys Ala Thr Gln Arg Leu Ala Asn Phe Leu Val His Ser Gly Asn Asn
            20                  25                  30

Phe Gly Ala Ile Leu Ser Ser Thr Asn Val Gly Ser Asn Thr Tyr Gly
        35                  40                  45

Lys Arg Asn Ala Val Glu Val Leu Lys Arg Glu Pro Leu Asn Tyr Leu
    50                  55                  60

Pro Leu
65

<210> SEQ ID NO 12
<211> LENGTH: 37
<212> TYPE: PRT
<213> ORGANISM: Homo sapiens

<400> SEQUENCE: 12

Lys Cys Asn Thr Ala Thr Cys Ala Thr Gln Arg Leu Ala Asn Phe Leu
1               5                   10                  15

Val His Ser Gly Asn Asn Phe Gly Ala Ile Leu Ser Ser Thr Asn Val
            20                  25                  30

Gly Ser Asn Thr Tyr
        35

<210> SEQ ID NO 13

<211> LENGTH: 10435
<212> TYPE: DNA
<213> ORGANISM: Artificial Sequence
<220> FEATURE:
<223> OTHER INFORMATION: Targeting construct

<400> SEQUENCE: 13

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | tagggttcc | tgcggccgct | ctgtacagga | caagatatga | gagtatatac | 180 |
| cataaggttt | cacatgaatt | cttaaaatac | ttactcttag | caaagacaca | gataatgaag | 240 |
| tactccccat | acaaaataaa | tacattgaga | taaaatctac | tgcattttgc | ctcaaattac | 300 |
| atatatccac | tggcatctgg | acgttgaatg | aagcttcata | cctcttgtcc | actttataat | 360 |
| taacctaaat | ttaactaata | ttttggttcc | tgtagagctg | aaaatgaaaa | catttctcta | 420 |
| gagttcctaa | taatccgcaa | aaggcaatgt | tataattctg | tatcaatttc | cagggctatt | 480 |
| gtgagagcgc | actgaaacaa | aaggtcatac | aaacatacgg | aattaacata | aataaattaa | 540 |
| cgcaaataaa | ttctgagatg | ttacaattga | aatgaattat | ttaacctggt | tatcacttct | 600 |
| gacttatcca | taatatttct | atgcagttat | tccgggtggc | tgcgtaatat | ggtgactatt | 660 |
| aataccattg | acataaaaag | ccttttggtt | ttaacaccta | acccaatcct | atcagtaaaa | 720 |
| ctgctgaaag | cataggaacc | aagcaggggt | ataagaacat | ggtaatcttc | atgtatttat | 780 |
| gctaagagta | atagaattcc | caccctacaa | tagtcagagt | acctgaacag | gaatttgatt | 840 |
| cccttgagaa | tttataatat | ctgacatttc | tcttaacact | cttgattcaa | gatctccaag | 900 |
| aacttaacag | aaattaacat | tggtcattct | gtgtgaaatg | tgtaggaagt | gaatatctat | 960 |
| ttttttaatt | cagcaagttc | caggttactt | attagtttac | attctaaatc | cttttttaaa | 1020 |
| aaaattggga | aatagattca | caaatatttt | aaaaaataga | agacaaagat | attttaatt | 1080 |
| attattttct | ggaatatatt | ctgaatttcc | aagaaaagga | ttgtactggg | aaattcaaca | 1140 |
| agtgaattcg | agctcggtac | ccggggatcc | cccaaccact | ccaagtggag | gctgagaaag | 1200 |
| gttttgtagc | tgggtagagt | atgtactaag | agatggagac | agctggctct | gagctctgaa | 1260 |
| gcaagcacct | cttatggaga | gttgctgacc | ttcaggtgca | aatctaagat | actacaggag | 1320 |
| aatacaccat | ggggcttcag | cccagttgac | tcccgagtgg | gctatgggtt | tgtggaagga | 1380 |
| gagatagaag | agaagggacc | tttcttcttg | aattctgctt | tccttctacc | tctgagggtg | 1440 |
| agctggggtc | tcagctgagg | tgaggacaca | gctatcagtg | gaactgtga | acaacagtt | 1500 |
| caagggacaa | agttactagg | tcccccaaca | actgcagcct | cctggggaat | gatgtggaaa | 1560 |
| aatgctcagc | caaggacaaa | gaaggcctca | ccctctctga | acaatgtcc | cctgctgtga | 1620 |
| actggttcat | caggccaccc | aggagcccct | attaagactc | taattaccct | aaggctaagt | 1680 |
| agaggtgttg | ttgtccaatg | agcactttct | gcagacctag | caccaggcaa | gtgtttggaa | 1740 |
| actgcagctt | cagcccctct | ggccatctgc | tgatccaccc | ttaatgggac | aaacagcaaa | 1800 |
| gtccaggggt | caggggggg | gtgctttgga | ctataaagct | agtggggatt | cagtaacccc | 1860 |
| ctctaaagct | tgatggggct | gagaacttca | gggtgagttt | ggggacccctt | gattgttctt | 1920 |
| tcttttcgc | tattgtaaaa | ttcatgttat | atggagggg | caagttttc | agggtgttgt | 1980 |
| ttagaatggg | aagatgtccc | ttgtatcacc | atggaccctc | atgataattt | tgtttctttc | 2040 |
| actttctact | ctgttgacaa | ccattgtctc | ctcttatttt | cttttcattt | tctgtaacttt | 2100 |
| tttcgttaaa | ctttagcttg | catttgtaac | gaatttttaa | attcactttt | gtttatttgt | 2160 |

```
cagattgtaa gtactttctc taatcacttt tttttcaagg caatcagggt atattatatt    2220
gtacttcagc acagttttag agaacaattg ttataattaa atgataaggt agaatatttc    2280
tgcatataaa ttctggctgg cgtggaaata ttcttattgg tagaaacaac tacatcctgg    2340
tcatcatcct gcctttctct ttatggttac aatgatatac actgtttgag atgaggataa    2400
aatactctga gtccaaaccg ggccctctg ctaaccatgt tcatgccttc ttctctttcc     2460
tacagctcct gggcaacgtg ctggttgttg tgctgtctca tcattttggc aaagaattca    2520
ccatgaagtt cctattctct agaaagtata ggaacttcgg catcctgaag ctgcaagtat    2580
ttctcattgt gctctctgtt gcattgaacc atctgaaagc tacacccatt gaaagtcatc    2640
aggtggaaaa gcggaaatgc aacactgcca catgtgcaac gcagcgcctg gcaaattttt    2700
tagttcattc cggcaacaac tttggtgcca ttctctcatc taccaacgtg ggatccaata    2760
catatggcaa gaggaatgca gtagaggttt aaagagaga gccactgaat tacttgcccc     2820
tttagaaggg cgaataacgt gctaaaggga acaaaagctg gagctccacc gcggataact    2880
tcgtatagca tacattatac gaagttatcg cgccctaccg ggtagggag cgcttttcc     2940 caaggcagtc tggagcatgc gctttagcag ccccgctggg cacttggcgc tacacaagtg    3000
gcctctggcc tcgcacacat tccacatcca ccggtaggcg ccaaccggct ccgttctttg    3060 gtggccctt cgcgccacct tctactcctc ccctagtcag gaagttcccc cccgccccgc     3120
agctcgcgtc gtgcaggacg tgacaaatgg aagtagcacg tctcactagt ctcgtgcaga    3180
tggacagcac cgctgagcaa tggaagcggg taggcctttg gggcagcggc caatagcagc    3240
tttggctcct tcgctttctg ggctcagagg ctgggaaggg gtgggtccgg gggcgggctc    3300
aggggcgggc tcaggggcgg ggcgggcgcc cgaaggtcct ccggaagccc ggcattctgc    3360
acgcttcaaa agcgcacgtc tgccgcgctg ttctcctctt cctcatctcc gggcctttcg    3420
acctgcagcc aatatgggat cggccattga acaagatgga ttgcacgcag gttctccggc    3480
cgcttgggtg gagaggctat tcggctatga ctgggcacaa cagacaatcg gctgctctga    3540
tgccgccgtg ttccggctgt cagcgcaggg gcgcccggtt ctttttgtca agaccgacct    3600
gtccggtgcc ctgaatgaac tgcaggacga ggcagcgcgg ctatcgtggc tggccacgac    3660
gggcgttcct tgcgcagctg tgctcgacgt tgtcactgaa gcgggaaggg actggctgct    3720
attgggcgaa gtgccggggc aggatctcct gtcatctcac cttgctcctg ccgagaaagt    3780
atccatcatg gctgatgcaa tgcggcggct gcatacgctt gatccggcta cctgcccatt    3840
cgaccaccaa gcgaaacatc gcatcgagcg agcacgtact cggatggaag ccggtcttgt    3900
caatcaggat gatctggacg aagagcatca ggggctcgcg ccagccgaac tgttcgccag    3960
gctcaaggcg cgcatgcccg acggcgagga tctcgtcgtg acccatggcg atgcctgctt    4020
gccgaatatc atggtggaaa atggccgctt ttctggattc atcgactgtg gccggctggg    4080
tgtggcggat cgctatcagg acatagcgtt ggctacccgt gatattgctg aagagcttgg    4140
cggcgaatgg gctgaccgct tcctcgtgct ttacggtatc gccgctcccg attcgcagcg    4200
catcgccttc tatcgccttc ttgacgagtt cttctgagat atcgtcgacg atatcataac    4260
ttcgtatagc atacattata cgaagttatt gaattcctgc agcccggggg atccgcccct    4320
ctccctcccc ccccctaac gttactggcc gaagccgctt ggaataaggc cggtgtgcgt    4380
ttgtctatat gttattttcc accatattgc cgtcttttgg caatgtgagg gcccggaaac    4440
ctggccctgt cttcttgacg agcattccta ggggtctttc ccctctcgcc aaaggaatgc    4500
```

```
aaggtctgtt gaatgtcgtg aaggaagcag ttcctctgga agcttcttga agacaaacaa    4560
cgtctgtagc gacccttttgc aggcagcgga accccccacc tggcgacagg tgcctctgcg    4620
gccaaaagcc acgtgtataa gatacacctg caaaggcggc acaaccccag tgccacgttg    4680
tgagttggat agttgtggaa agagtcaaat ggctctcctc aagcgtattc aacaaggggc    4740
tgaaggatgc ccagaaggta ccccattgta tgggatctga tctggggcct cggtgcacat    4800
gctttacatg tgtttagtcg aggttaaaaa aacgtctagg ccccccgaac cacggggacg    4860
tggttttcct ttgaaaaaca cgatgataat atggccacag aagttcctat tcttcaaata    4920
gtataggaac ttcaccatgg tgcacgtgga tccaaaaaag aagagaaagg tagatccaaa    4980
aaagaagaga aaggtagatc caaaaaagaa gagaaaggta cacgtgtcca tggtgagcaa    5040
gggcgaggag ctgttcaccg gggtggtgcc catcctggtc gagctggacg gcgacgtaaa    5100
cggccacaag ttcagcgtgt ccggcgaggg cgagggcgat gccacctacg gcaagctgac    5160
cctgaagttc atctgcacca ccggcaagct gcccgtgccc tggcccaccc tcgtgaccac    5220
cctgacctac ggcgtgcagt gcttcagccg ctaccccgac cacatgaagc agcacgactt    5280
cttcaagtcc gccatgcccg aaggctacgt ccaggagcgc accatcttct tcaaggacga    5340
cggcaactac aagacccgcg ccgaggtgaa gttcgagggc gacaccctgg tgaaccgcat    5400
cgagctgaag ggcatcgact tcaaggagga cggcaacatc ctggggcaca agctggagta    5460
caactacaac agccacaacg tctatatcat ggccgacaag cagaagaacg gcatcaaggt    5520
gaacttcaag atccgccaca acatcgagga cggcagcgtg cagctcgccg accactacca    5580
gcagaacacc cccatcggcg acggccccgt gctgctgccc gacaaccact acctgagcac    5640
ccagtccgcc ctgagcaaag accccaacga aagcgcgat cacatggtcc tgctggagtt    5700
cgtgaccgcc gccgggatca ctctcggcat ggacgagctg tacaagtaaa ggtcaacgca    5760
cctctaaagt tcttattgct ttatgtataa atccctagt gatttcctgt ataatttaac    5820 agtaccttt tcatttctaa agtgaatatg tgaatctgtg tgtcccatgt ttgctgccag    5880
tacatgtaaa ctgttgtgct gagaattgtt ttaaatttaa tactaatcaa gatcccttaa    5940
taaaaaggca aagtctttac aaatgaaata ttcttcctgt agatttttat ttaaaaaaaa    6000
aaaaacattt taaaaagtca tttatttttt cctgtatatt tatgacctga gttttccaac    6060
aaaggaggaa atggttgttg gcaacttggt aaactgtaaa cagctaatag taaagttatg    6120
atgctgaaca ttagaaaatc agcaattatt agtacccttg ataagcaatc tcttttgcat    6180
tcaatttatg aaatgagata aaatgttgtt taaaaaaaat aaagactgct cctgactcag    6240
tcaaaatatt ttttaaaact ctggttttgt ttgtacttgc tgatactaag agtttactta    6300
aaaatataaa acccaatttg cgtccatgag gatttcactg tgtttcatca acagtgggct    6360
tttattaaat gtatatgcct tttattctat ttaagtggct ttcagcaaat ctttgtcata    6420
tttttataca gagtgctgta ccagcaagta aacaaaaaaa gcaaaaacaa caaactttat    6480
aatttggtaa tcttaaggca tacttcataa ggggaaattt ttatgtattt atacataaat    6540
accctagtga tttcctgtta ctatgaaact tattccaacc aggagacttg agaaggaaag    6600
aagctattac cttgataaaa taggtattaa tagtagatat tattctaaag tttattcatt    6660
aaaattatta tcaaagtgaa acgtgaacaa aatcagaatt atttcctcag ttgatattcc    6720
taggccagta ggaatctaag tatatgaacc ttgggaatac gagactgcca tggagtgccc    6780
caaatacttt ccctggtttc tcataattac cttgtgaaat aataatgagc ttttcttttat    6840 tgatataact ggagatagca acagtaagtt ttggtggcta atttcatccc atctttttctc    6900
```

```
attgtatcta ccatgcttga aatcataggt acccttggat aatcttccaa atacttatgt    6960
acatgctaca aattatattt tattgaagtt ttagaaacac aaatgattct tctatctccc    7020
atgttgcaat acagagtcag gacaaataat ttattaatta atactgtgtt taaaatttct    7080 agggcccttaa aaaaaaaga caaagggagt tcccatcgtg gctcagcaga aacaaatcag    7140
actggcatcc atgaggaagc aggttccatc cctggctttg ctcagtgggt tcaggatctg    7200
gcgttgctgt gagctgttgg gtagattgca gacatggctc agatctgaca ttgctgtggc    7260
tgtggtgtag gctggcggct acagctctga tttgacccct agtctgggaa tggccatatg    7320
ccatgggtgt cgcccttaaa aaaaagaaa agaaaacaac tagaaattct cctgatcatt     7380
gtgagatgac attctgcaat aagcctcata cttcgctgag gggttgaata tcattacctc    7440
atgaaatatg cttagataaa gaatacccttt tggttaagag tagaaaagcc tatgagtcta   7500
aagctcctta ggctgagtgc agagagagct tttcatgcaa agtagaatat tttcttttttc  7560 taaccattat cccctcaccc tctgggcatt tacacccagg ttctactcaa atgccacatt    7620
ctgcaaggaa cttgtctgaa cttacataga ttttttatcta tattttctga caccagttta   7680
ttcagacatg cggccgcagg aacccctagt gatggagttg gccactccct ctctgcgcgc    7740
tcgctcgctc actgaggccg ggcgaccaaa ggtcgcccga cgcccgggct ttgcccgggc    7800
ggcctcagtg agcgagcgag cgcgcagctg cctgcagggg cgcctgatgc ggtattttct    7860
ccttacgcat ctgtgcggta tttcacaccg catacgtcaa agcaaccata gtacgcgccc    7920
tgtagcggcg cattaagcgc ggcgggtgtg gtggttacgc gcagcgtgac cgctacactt    7980
gccagcgccc tagcgcccgc tcctttcgct ttcttccctt cctttctcgc cacgttcgcc    8040
ggctttcccc gtcaagctct aaatcggggg ctccctttag ggttccgatt tagtgcttta    8100
cggcacctcg accccaaaaa acttgatttg ggtgatggtt cacgtagtgg gccatcgccc    8160
tgatagacgg ttttttcgccc tttgacgttg gagtccacgt tctttaatag tggactcttg    8220
ttccaaactg gaacaacact caaccctatc tcgggctatt cttttgattt ataagggatt    8280
ttgccgattt cggcctattg gttaaaaaat gagctgattt aacaaaaatt taacgcgaat    8340
tttaacaaaa tattaacgtt tacaatttta tggtgcactc tcagtacaat ctgctctgat    8400
gccgcatagt taagccagcc ccgacacccg ccaacacccg ctgacgcgcc ctgacgggct    8460
tgtctgctcc cggcatccgc ttacagacaa gctgtgaccg tctccgggag ctgcatgtgt    8520
cagaggtttt caccgtcatc accgaaacgc gcgagacgaa agggcctcgt gatacgccta    8580
tttttatagg ttaatgtcat gataataatg gtttcttaga cgtcaggtgg cacttttcgg    8640
ggaaatgtgc gcggaacccc tatttgttta ttttttctaaa tacattcaaa tatgtatccg   8700
ctcatgagac aataaccctg ataaatgctt caataatatt gaaaaaggaa gagtatgagt    8760
attcaacatt tccgtgtcgc ccttattccc ttttttgcgg cattttgcct tcctgttttt    8820
gctcacccag aaacgctggt gaaagtaaaa gatgctgaag atcagttggg tgcacgagtg    8880
ggttacatcg aactggatct caacagcggt aagatccttg agagttttcg ccccgaagaa    8940
cgttttccaa tgatgagcac ttttaaagtt ctgctatgtg gcgcggtatt atcccgtatt    9000
gacgccgggc aagagcaact cggtcgccgc atacactatt ctcagaatga cttggttgag    9060
tactcaccag tcacagaaaa gcatcttacg gatggcatga cagtaagaga attatgcagt    9120
gctgccataa ccatgagtga taacactgcg gccaacttac ttctgacaac gatcggagga    9180
ccgaaggagc taaccgcttt tttgcacaac atgggggatc atgtaactcg ccttgatcgt    9240
```

-continued

```
tgggaaccgg agctgaatga agccatacca aacgacgagc gtgacaccac gatgcctgta    9300
gcaatggcaa caacgttgcg caaactatta actggcgaac tacttactct agcttcccgg    9360
caacaattaa tagactggat ggaggcggat aaagttgcag gaccacttct gcgctcggcc    9420
cttccggctg gctggtttat tgctgataaa tctggagccg gtgagcgtgg gtctcgcggt    9480
atcattgcag cactggggcc agatggtaag ccctcccgta tcgtagttat ctacacgacg    9540
gggagtcagg caactatgga tgaacgaaat agacagatcg ctgagatagg tgcctcactg    9600
attaagcatt ggtaactgtc agaccaagtt tactcatata tactttagat tgatttaaaa    9660
cttcattttt aatttaaaag gatctaggtg aagatccttt ttgataatct catgaccaaa    9720
atcccttaac gtgagttttc gttccactga gcgtcagacc ccgtagaaaa gatcaaagga    9780
tcttcttgag atccttttt tctgcgcgta atctgctgct tgcaaacaaa aaaaccaccg     9840
ctaccagcgg tggtttgttt gccggatcaa gagctaccaa ctctttttcc gaaggtaact    9900
ggcttcagca gagcgcagat accaaatact gtccttctag tgtagccgta gttaggccac    9960
cacttcaaga actctgtagc accgcctaca tacctcgctc tgctaatcct gttaccagtg    10020
gctgctgcca gtggcgataa gtcgtgtctt accgggttgg actcaagacg atagttaccg    10080
gataaggcgc agcggtcggg ctgaacgggg gttcgtgca cacagcccag cttggagcga     10140
acgacctaca ccgaactgag atacctacag cgtgagctat gagaaagcgc cacgcttccc    10200
gaagggagaa aggcggacag gtatccggta agcggcaggg tcggaacagg agagcgcacg    10260
agggagcttc caggggggaaa cgcctggtat ctttatagtc ctgtcgggtt tcgccacctc    10320
tgacttgagc gtcgatttt gtgatgctcg tcagggggc ggagcctatg gaaaaacgcc      10380
agcaacgcgg cctttttacg gttcctggcc ttttgctggc cttttgctca catgt         10435
```

<210> SEQ ID NO 14
<211> LENGTH: 50
<212> TYPE: DNA
<213> ORGANISM: Artificial sequence
<220> FEATURE:
<223> OTHER INFORMATION: TALEN-1
<220> FEATURE:
<221> NAME/KEY: misc_feature
<222> LOCATION: (1)..(50)
<223> OTHER INFORMATION: TALEN-1

<400> SEQUENCE: 14

```
tgctgtatga tttccaagca aaccaaaaca ctgggttact gataggaaga                50
```

<210> SEQ ID NO 15
<211> LENGTH: 50
<212> TYPE: DNA
<213> ORGANISM: Artificial sequence
<220> FEATURE:
<223> OTHER INFORMATION: TALEN-1
<220> FEATURE:
<221> NAME/KEY: misc_feature
<222> LOCATION: (1)..(50)
<223> OTHER INFORMATION: TALEN-1

<400> SEQUENCE: 15

```
tcttcctatc agtaacccag tgttttggtt tgcttggaaa tcatacagca                50
```

<210> SEQ ID NO 16
<211> LENGTH: 56
<212> TYPE: DNA
<213> ORGANISM: Artificial sequence
<220> FEATURE:
<223> OTHER INFORMATION: TALEN-2

-continued

```
<220> FEATURE:
<221> NAME/KEY: misc_feature
<222> LOCATION: (1)..(56)
<223> OTHER INFORMATION: TALEN-2

<400> SEQUENCE: 16
ttgtatccaa tcctgagtct aagtttctaa cctttcatat ttcttcgatg ttccca           56

<210> SEQ ID NO 17
<211> LENGTH: 56
<212> TYPE: DNA
<213> ORGANISM: Artificial sequence
<220> FEATURE:
<223> OTHER INFORMATION: TALEN-2
<220> FEATURE:
<221> NAME/KEY: misc_feature
<222> LOCATION: (1)..(56)
<223> OTHER INFORMATION: TALEN-2

<400> SEQUENCE: 17
tgggaacatc gaagaaatat gaaaggttag aaacttagac tcaggattgg atacaa           56
```

PIG MODEL FOR DIABETES

FIELD OF INVENTION

The present invention relates to a transgenic pig comprising a mutated IAPP gene and displaying a phenotype associated with diabetes. The invention also relates to a transgenic blastocyst, embryo, fetus, donor cell and/or cell nucleus derived from said transgenic pig. The invention further relates to use of the transgenic pig as a model system for studying therapy, treatment and/or prevention of diabetes.

BACKGROUND OF INVENTION

Diabetes is a complex group of diseases with a variety of causes. People with diabetes have high blood glucose, also called high blood sugar or hyperglycemia. Diabetes is a disorder of metabolism that develops when the body doesn't produce enough insulin or is not able to use insulin effectively, or both. Insulin is made in the pancreas, an organ located behind the stomach. The pancreas contains clusters of cells called islets. Beta cells within the islets make insulin and release it into the blood.

Type 1 diabetes is caused by a lack of insulin due to the destruction of insulin-producing beta cells in the pancreas. In type 1 diabetes—an autoimmune disease—the body's immune system attacks and destroys the beta cells. Normally, the immune system protects the body from infection by identifying and destroying bacteria, viruses, and other potentially harmful foreign substances. But in autoimmune diseases, the immune system attacks the body's own cells. In type 1 diabetes, beta cell destruction may take place over several years, but symptoms of the disease usually develop over a short period of time.

Type 2 diabetes mellitus (T2DM) is a complex and heterogeneous disorder involving many physiological risk factors and genetic susceptibility factors. It has long been noticed that humans, non-human primates, and cats are susceptible to spontaneous development of T2DM characterized by islet amyloid deposits while spontaneous T2DM is rare in rodents and pigs. One hypothesis is that formation of islet amyloid from islet amyloid polypeptide (IAPP) is a pathogenic factor for β-cell degeneration and apoptosis, which gradually causes T2DM (Matveyenko and Butler, 2006, ILAR J 47(3): 225-33). The major component of islet amyloid is formed by fibrils of IAPP, a 37-amino acid monomeric polypeptide synthesized by pancreatic β-cells. The residues 20-29 of IAPP are the most critical region for the amyloidogenic properties (Westermark et al., 1990, Proc Natl Acad Sci USA 87(13): 5036-40). In humans, monkeys and cats, IAPP is prone to form toxic amyloid aggregates, whereas IAPP from rodents and pigs is more refractory to amyloid formation (Zhang et al., 2011, FEBS Lett 585(1): 71-7). Furthermore, a susceptibility variant of the human IAPP gene (S20G) has been found to be associated with early onset Type 2 diabetes (T2DM) in Asian populations (Morita et al., 2011).

Animal models, such as rodents, rabbits, dogs, cats, pigs and primates, have been used extensively in T2DM research, investigating disease pathogenesis and testing preventions and therapies. With the advances in transgenic technologies, many transgenic, complete knockout and conditional knockout mice have been generated for diabetic research. Recently, gene knockout rats have been generated with Zinc-Finger Nucleases (ZFNs) for diabetic research (Geurts et al., 2009, Science 325(5939): 433). Nevertheless, rodents are still considered to be inadequate to reflect the pathogenesis of T2DM in humans. Thus, most clinical and translational research, including testing of prevention strategies and drugs, require large animal models such as pigs.

Several mouse models expressing human IAPP (hIAPP) have been created to study the pathogenesis of IAPP-associated T2DM. These hIAPP transgenic mice were generated by targeting the expression of IAPP to pancreatic β-cells using the rat insulin 2 promoter (RIP2) (Couce et al., 1996, Diabetes 45(8): 1094-101; Janson et al., 1996, Proc Natl Acad Sci USA 93(14): 7283-8). Spontaneous onset T2DM was observed in hIAPP homozygous mice. However, hIAPP hemizygous mice do not develop diabetes unless they have obese background or are treated with growth hormone. Several islet pathological phenotypes such as intra- and extracellular amyloid deposits, increased β-cell apoptosis, and decreased β-cell mass were observed in diabetic hIAPP mice. Based on the studies of hIAPP mouse models, dose dependent hIAPP expression is suggested to be a critical factor for β-cell toxicity and T2DM pathogenesis (Matveyenko and Butler, 2006, ILAR J 47(3): 225-33).

A transgenic rat model for human IAPP (HIP rat) was generated for studying T2DM pathogenesis associated with islet amyloid formation (Butler et al., 2004, Diabetes 53(6): 1509-16). Similar to hIAPP mice, the pathogenic process depended on the dose of hIAPP expression and the homozygous HIP rat developed diabetes between 5 and 10 months of age, displaying island amyloid and an approximately 60% deficit in β-cell mass. Thus, both mouse and rat diabetic hIAPP models developed islet pathology related to that in humans. Nevertheless, the rodent hIAPP models cannot fully address the pathogenic process of T2DM associated with islet amyloid formation by IAPP aggregation. Although IAPP pathology was reported to induce insulin resistance, insulin resistance was not observed in the rodent IAPP models.

One major weakness of previous mouse or rat IAPP models is that these animal models are still expressing their own IAPP gene. Previous study have shown that the presence of none aggregate IAPP peptide (e.g. the porcine IAPP peptide) can delay/prevent amyloid formation. This suggests that the discrepancy of diabetic phenotypes observed in the previous rodent IAPP models might be due to compensatory effects and/or anti-aggregation effects from endogenous IAPP. Thus, new animal models generated by targeted replacement of the endogenous IAPP gene (knockout) with amyloidogenic form of hIAPP (knockin) should represent a better model for studying IAPP's role in islet pathology of T2DM patients.

Pigs have been favoured as an animal model for T2DM due to the anatomical and physiological similarities of the pig and human pancreas and islets. Several pig models of chemically induced diabetes have been generated by streptozotocin administration. Most importantly, the generation of transgenic (GM) pigs for diabetic research has now become possible by cloning based on somatic cell nuclear transfer (SCNT). The first GM pig model for T2DM was a transgenic pig expressing a dominant negative mutant form of the glucose-dependent insulinotropic polypeptide (GIP) receptor (GIPRdn) in pancreatic cells. It was generated in the laboratory of Eckhard Wolf in Munich (Renner et al., 2010, Diabetes 59(5): 1228-38). Similar to the GIPRdn mice, the GIPRdn pigs exhibited significant oral glucose tolerance reduction and β-cell proliferation reduction by the age of 11 weeks. Glucose control deterioration and reduction of β-cell mass were observed in the GIPRdn pigs with increasing age (Renner et al., 2010, Diabetes 59(5): 1228-

38). Another successful GM pig model of diabetes was a transgenic pig expressing a dominant negative mutant hepatocyte nuclear factor 1α (HNF1AP291fsinsC) gene. The HNF1AP291fsinsC pigs developed diabetes at the age of 20-196 days, characterized by non-fasting blood glucose higher than 200 mg/dl, as well as small and irregularly formed Langerhans Islets (Umeyama et al., 2009, Transgenic Res 18(5): 697-706). The successful modeling of human diabetes in the GIPRdn and HNF1AP291fsinsC pigs has provided proof of concept for the future development of other GM pig models for the human disease.

SUMMARY OF INVENTION

A main object of the present invention is to provide an animal model that can be used for the study of diabetes. The animal model presented herein is a transgenic pig having a mutated Islet Amyloid Polypeptide (IAPP) gene.

In one aspect the present invention relates to a transgenic pig comprising a mutated Islet Amyloid Polypeptide (IAPP) gene or part thereof and displaying at least one phenotype associated with diabetes.

In a preferred embodiment the mutated IAPP gene is a human mutated IAPP gene or part thereof. In a particular embodiment thereof, said mutated human IAPP gene said mutated IAPP gene comprises a mutation resulting in the amino acid substitution S20G.

It is preferred that the transgenic pig as described herein does not express a pig IAPP gene. In particular, it is preferred that the transgenic pig does not express an endogenous pig IAPP gene. More specifically, it is preferred that said endogenous pig IAPP gene has been knocked out.

The transgenic pig of the present invention can be any pig. In a preferred embodiment of the present invention the transgenic pig is a mini-pig. In particular, the mini-pig may be a Goettingen mini-pig. In another embodiment the transgenic pig is an inbred pig.

The transgenic pig provided by the present invention display at least one phenotype associated with or related to diabetes. It is preferred that the transgenic pig displays higher glucose levels, higher glucagon levels lower insulin levels and/or lower c-peptide levels when compared to a control pig. It is preferred that said control pig does not comprise a mutated IAPP gene.

In one embodiment said glucose level is increased by at least 10% when compared to a control pig and wherein said transgenic pig and said control pig are given a normal diet. In another embodiment said glucagon level is increased by at least 10% when compared to a control pig and wherein said transgenic pig and said control pig are given a normal diet. In yet another embodiment said insulin level is decreased by at least 10% when compared to a control pig and wherein said transgenic pig and said control pig are given a normal diet. In a further embodiment said c-peptide level is decreased by at least 10% when compared to a control pig and wherein said transgenic pig and said control pig are given a normal diet.

It is preferred that the transgenic pig as described herein displays hyperglycemia. Thus, in one embodiment the least one phenotype is hyperglycemia. In another embodiment the transgenic pig displays β-cell degeneration. Thus, in another embodiment the least one phenotype is β-cell degeneration In one embodiment the transgenic pig as described herein displays at least one phenotype selected from the group consisting of blindness, inflammation, infection and organ deformation. Thus, in a further embodiment said at least one phenotype is selected from the group consisting of blindness, inflammation, infection and organ deformation.

The present invention also relates to a transgenic blastocyst, embryo, fetus, donor cell and/or cell nucleus derived from the transgenic pig according to the present invention.

Another aspect of the present invention relates to a method for producing the transgenic pig as described herein, said method comprising:
  i. producing an oocyte having a partially modified zona pellucida
  ii. separating the oocyte into at least two parts obtaining an oocyte having a nucleus and at least one cytoplast
  iii. producing a donor cell comprising a mutated IAPP gene or part thereof
  iv. fusing at least one cytoplast with the donor cell or membrane surrounded cell nucleus
  v. obtaining a reconstructed embryo,
  vi. activating the reconstructed embryo to form an embryo, culturing said embryo and
  vii. transferring said cultured embryo to a host mammal, wherein the embryo develops into a transgenic pig.

It is appreciated that said method does not involve a surgical step. In one preferred embodiment the donor cell comprises a mutated IAPP gene, wherein the mutated IAPP gene is a human mutated IAPP gene. In particular, said mutated IAPP gene comprises an S20G mutation. It is further preferred that the donor cell does not express an endogenous pig IAPP gene. In a specific embodiment the endogenous pig IAPP gene has been knocked out.

A further aspect of the present invention relates to use of the transgenic pig as a model system for studying therapy, treatment and/or prevention of diabetes.

The pigs can also be used for identifying compounds suitable for the therapy, treatment and/or prevention of diabetes. Such a method preferably comprises the following steps
(i) providing a transgenic pig according to the present invention,
(ii) providing a compound to be tested,
(iii) administering said compound to said transgenic pig,
(iv) determining the insulin level, glucose level and/or glucagon level of said transgenic pig,
thereby determining the effect of said compound on the insulin level, glucose level, glucagon level and/or c-peptide level of said transgenic pig.

Also provided is a method for studying therapy, treatment and/or prevention of diabetes by applying the transgenic pig according to the present invention.

In another aspect the invention relates to a method for studying therapy, treatment and/or prevention of diabetes comprising the steps of
  i. providing a transgenic pig according to any of claims 1 to 16
  ii. providing a compound to be tested,
  iii. administering said compound to said transgenic pig,
  iv. determining risk factors associated with diabetes, such as the insulin level, glucose level and/or glucagon level of said transgenic pig,
  thereby determining the effect of said compound on the insulin level, glucose level, glucagon level and/or c-peptide level of said transgenic pig.

DETAILED DESCRIPTION OF THE INVENTION

Figure 1:
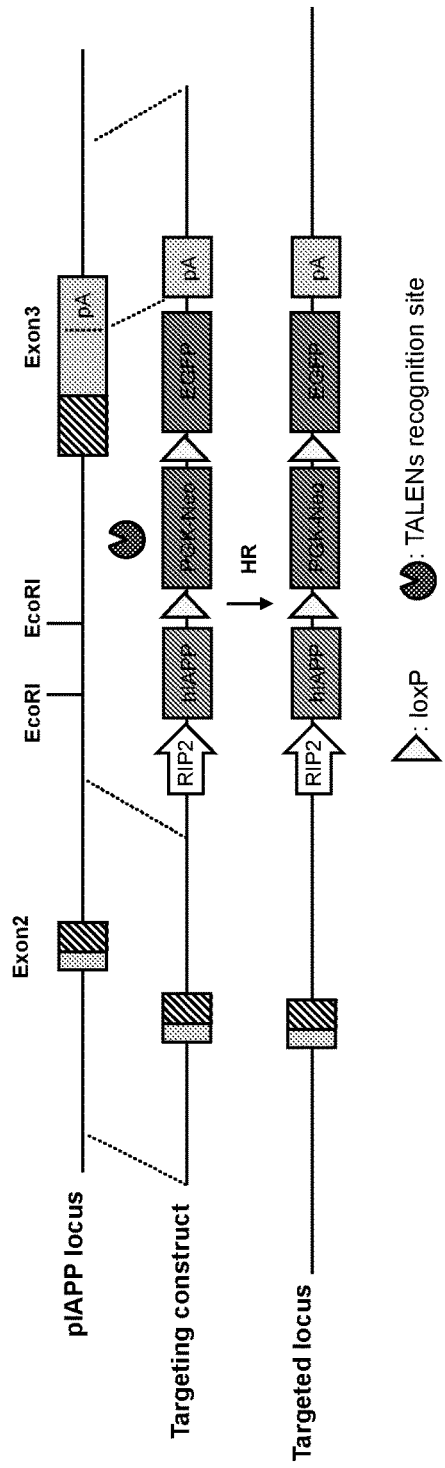
FIG. 1. Schematic representation of pIAPP knockout/hIAPP knockin (pIAPPKO;hIAPPKI) construct. RIP, rat insulin promoter; PGK, Phosphoglycerate kinase I promoter; Neo, neomycin resistant maker; EGFP, enhanced green fluorescent protein; pA, poly A signal, HR, homologous recombination.

It is within the scope of the present invention to provide an animal model that can be used for the study of diabetes. The animal model presented herein is a transgenic pig having a mutated IAPP gene. These transgenic pigs display phenotypes that resemble phenotypes observed in human diabetes. The transgenic pigs having a mutated IAPP gene as presented herein therefore represent an ideal animal model for the study of human diabetes.

Thus, a first aspect of the present invention relates to a transgenic pig comprising a mutated Islet Amyloid Polypeptide (IAPP) gene or part thereof and displaying at least one phenotype associated with diabetes.

The term "transgenic pig" as used herein refers to a pig comprising a foreign gene or an altered gene sequence. This gene may be present on a plasmid. However, it is preferred that the foreign gene is inserted into the genome of the pig. It is also preferred that the gene is expressed, i.e. that the pig expresses the protein encoded by the foreign gene. In the present invention the foreign or altered gene is a mutated IAPP gene.

It will be appreciated that the invention does not comprise processes for modifying the genetic identity of pigs in a way, which is likely to cause them suffering without any substantial medical benefit to man or animal, or animals resulting from such processes.

The methods for producing the transgenic pig described herein need not encompass a surgical step performed on the pig.

The IAPP Gene

The transgenic pig of the present invention comprises a mutated Islet Amyloid Polypeptide (IAPP) gene. Islet Amyloid Polypeptide, also called amylin, is produced by the pancreatic β-cells and secreted in parallel with insulin. In human, Islet Amyloid Polypeptide is co-secreted with insulin from the pancreatic β-cells in the ratio of approximately 100:1. In for example human, monkeys and cats, IAPP has a tendency to aggregate and form toxic amyloid aggregates. The aggregation seems to be toxic by for example leading to β-cell degeneration and diabetes. IAPP from for example rodents and pigs is more refractory to amyloid aggregate formation. Thus, in a preferred embodiment, the mutated Islet Amyloid Polypeptide (IAPP) gene is from an organism wherein the IAPP gene has a tendency to form amyloid aggregates. In one embodiment the mutated IAPP gene is a mutated monkey IAPP gene or part thereof or a mutated cat IAPP gene or part thereof.

In a preferred embodiment the mutated IAPP gene is a human mutated IAPP gene or part thereof. The human IAPP gene (SEQ ID NO:1) encodes a 89-amino acids residue protein (SEQ ID NO:4), which consists of a 22 amino acids signal peptide and a 67 amino acids pro-peptide also known as proIAPP, Proamylin or Proislet Protein (SEQ ID NO:5). When released from the signal peptide, proamylin undergoes post-translational modifications including protease cleavage to produce the biologically active amylin consisting of 37 amino acids (SEQ ID NO:6).

The nucleotide sequence of the wild type human IAPP gene encoding the 89 amino acid residues peptide has SEQ ID NO:1.

Thus, in one embodiment, the transgenic pig of the present invention comprises a human mutated IAPP gene having at least 70% sequence identity with SEQ ID NO:1, such as for example at least 75% sequence identity with SEQ ID NO:1, such as at least 80% sequence identity with SEQ ID NO:1, such as for example at least 85% sequence identity with SEQ ID NO:1, such as at least 90% sequence identity with SEQ ID NO:1, such as at least 95% sequence identity with SEQ ID NO:1, such as for example at least 97% sequence identity with SEQ ID NO:1 or such as at least 99% sequence identity with SEQ ID NO:1 or part thereof.

The nucleotide sequence of the wild type human IAPP gene encoding the 67 amino acids proamylin protein has SEQ ID NO:2.

Thus, in one embodiment, the transgenic pig of the present invention comprises a human mutated IAPP gene having at least 70% sequence identity with SEQ ID NO:2, such as for example at least 75% sequence identity with SEQ ID NO:2, such as at least 80% sequence identity with SEQ ID NO:2, such as for example at least 85% sequence identity with SEQ ID NO:2, such as at least 90% sequence identity with SEQ ID NO:2, such as at least 95% sequence identity with SEQ ID NO:2, such as for example at least 97% sequence identity with SEQ ID NO:2 or such as at least 99% sequence identity with SEQ ID NO:2 or part thereof.

The nucleotide sequence of the wild type human IAPP gene encoding the 37 amino acids amylin protein has SEQ ID NO:3.

Thus, in another embodiment, the transgenic pig of the present invention comprises a human mutated IAPP gene having at least 70% sequence identity with SEQ ID NO:3, such as for example at least 75% sequence identity with SEQ ID NO:3, such as at least 80% sequence identity with SEQ ID NO:3, such as for example at least 85% sequence identity with SEQ ID NO:3, such as at least 90% sequence identity with SEQ ID NO:3, such as at least 95% sequence identity with SEQ ID NO:3, such as for example at least 97% sequence identity with SEQ ID NO:3 or such as at least 99% sequence identity with SEQ ID NO:3 or part thereof.

The transgenic pig of the present invention may comprise a human mutated IAPP gene having at least 70% sequence identity with SEQ ID NO:1, SEQ ID NO:2 or SEQ ID NO:3, such as for example at least 75% sequence identity with SEQ ID NO:1, SEQ ID NO:2 or SEQ ID NO:3, such as at least 80% sequence identity with SEQ ID NO:1, SEQ ID NO:2 or SEQ ID NO:3, such as for example at least 85% sequence identity with SEQ ID NO:3, such as at least 90% sequence identity with SEQ ID NO:1, SEQ ID NO:2 or SEQ ID NO:3, such as at least 95% sequence identity with SEQ ID NO:1, SEQ ID NO:2 or SEQ ID NO:3, such as for example at least 97% sequence identity with SEQ ID NO:1, SEQ ID NO:2 or SEQ ID NO:3 or such as at least 99% sequence identity with SEQ ID NO:1, SEQ ID NO:2 or SEQ ID NO:3 or part thereof.

The mutated IAPP gene may comprise one or more mutations. The IAPP gene comprises at least one mutation. In one preferred embodiment the IAPP gene comprises one mutation. In another embodiment the IAPP gene comprises two mutations. The IAPP gene may also comprise 3, 4, 5, 6, 7, 8, 9 or 10 mutations.

The mutation may be any kind of mutation. In one embodiment the at least one mutation is a deletion of one or more nucleotides, such as for example at least 1 nucleotide, such as at least 2 nucleotides, at least 3 nucleotides, such as for example at least 4 nucleotides, such as at least 5 nucleotide s, at least 6 nucleotides, such as for example at least 7 nucleotides, such as at least 8 nucleotides, at least 9 nucleotides, such as for example at least 10 nucleotides, such as at least 11 nucleotides, at least 12 nucleotides, such as for example at least 13 nucleotides, such as at least 14 nucleotides, at least 15 nucleotides or such as for example at least 20 nucleotides.

In another embodiment the at least one mutation is an insertion of one or more nucleotides, such as for example at least 1 nucleotide, such as at least 2 nucleotides, at least 3 nucleotides, such as for example at least 4 nucleotides, such as at least 5 nucleotides, at least 6 nucleotides, such as for example at least 7 nucleotides, such as at least 8 nucleotides, at least 9 nucleotides, such as for example at least 10 nucleotides, such as at least 11 nucleotides, at least 12 nucleotides, such as for example at least 13 nucleotides, such as at least 14 nucleotides, at least 15 nucleotides or such as for example at least 20 nucleotides.

In a preferred embodiment the at least one mutation is a point mutation. In a point mutation a single nucleotide is exchanged for another. The point mutation may be an A>G mutation, an A>C mutation, an A>T mutation, a T>G mutation, a T>C mutation, a T>A mutation, a G>T mutation, a G>C mutation, n G>A mutation, a C>G mutation, a C>T mutation or a C>A mutation. An A>G mutation means that adenine is replaced by guanine. In a more preferred embodiment the point mutation is a missense mutation in which a single nucleotide is changed, resulting in a codon that codes for a different amino acid. Thus in a preferred embodiment the isolated polynucleotide according to the present invention comprises at least one mutation that results in an amino acid substitution.

In a particular embodiment the isolated polynucleotide according to the present invention comprises a mutation resulting in the amino acid substitution S20G. S20G means that serine at amino acid position 20 of SEQ ID NO: 9 (active amylin) has been substituted with glycine. In SEQ ID NO:8 the corresponding serine residue is located at amino acid position 30, whereas in SEQ ID NO:7 the corresponding serine residue is located at amino acid position 51.

Thus, in a preferred embodiment the transgenic pig comprises a mutated IAPP gene comprising a mutation that results in the amino acid substitution A20G, wherein serine at amino acid position 20 of the 37 amino acid amylin protein is replaced by glycine. Codon 157AGC positioned at nucleotides 157-159 of SEQ ID NO:1, codon 91AGC positioned at nucleotides 91-93 of SEQ ID NO:2, and codon 58AGC positioned at nucleotides 58-60 of SEQ ID NO:3 encode said serine.

The codons of glycine are GGT, GGC, GGA or GGG. Thus it is preferred that codon AGC encoding serine 20 of wild type human amylin is replaced by GGT, GGC, GGA or GGG.

In a preferred embodiment the human mutated IAPP gene comprises the mutation A157G wherein the adenine at position 157 of SEQ ID NO:1 is replaced by guanine. The sequence comprising the mutation A157AG is SEQ ID NO: 4.

Thus, in one embodiment, the transgenic pig of the present invention comprises a human mutated IAPP gene having at least 70% sequence identity with SEQ ID NO:4, such as for example at least 75% sequence identity with SEQ ID NO:4, such as at least 80% sequence identity with SEQ ID NO:4, such as for example at least 85% sequence identity with SEQ ID NO:4, such as at least 90% sequence identity with SEQ ID NO:4, such as at least 95% sequence identity with SEQ ID NO:4, such as for example at least 97% sequence identity with SEQ ID NO:4 or such as at least 99% sequence identity with SEQ ID NO:4 or part thereof.

In a preferred embodiment the human mutated IAPP gene comprises the mutation A91G wherein the adenine at position 91 of SEQ ID NO:1 is replaced by guanine. The sequence comprising the mutation A91G is SEQ ID NO: 5.

Thus, in one embodiment, the transgenic pig of the present invention comprises a human mutated IAPP gene having at least 70% sequence identity with SEQ ID NO:5, such as for example at least 75% sequence identity with SEQ ID NO:5, such as at least 80% sequence identity with SEQ ID NO:5, such as for example at least 85% sequence identity with SEQ ID NO:5, such as at least 90% sequence identity with SEQ ID NO:5, such as at least 95% sequence identity with SEQ ID NO:5, such as for example at least 97% sequence identity with SEQ ID NO:5 or such as at least 99% sequence identity with SEQ ID NO:5 or part thereof.

In a preferred embodiment the human mutated IAPP gene comprises the mutation 58A>G wherein the adenine at position 58 of SEQ ID NO:1 is replaced by guanine. The sequence comprising the mutation 58A>G is SEQ ID NO: 6.

Thus, in one embodiment, the transgenic pig of the present invention comprises a human mutated IAPP gene having at least 70% sequence identity with SEQ ID NO:6, such as for example at least 75% sequence identity with SEQ ID NO:6, such as at least 80% sequence identity with SEQ ID NO:6, such as for example at least 85% sequence identity with SEQ ID NO:6, such as at least 90% sequence identity with SEQ ID NO:6, such as at least 95% sequence identity with SEQ ID NO:6, such as for example at least 97% sequence identity with SEQ ID NO:6 or such as at least 99% sequence identity with SEQ ID NO:6 or part thereof.

In one embodiment the transgenic pig of the present invention comprises a human mutated IAPP gene having at least 70% sequence identity with SEQ ID NO:4, SEQ ID NO:5 or SEQ ID NO:6, such as for example at least 75% sequence identity with SEQ ID NO:4, SEQ ID NO:5 or SEQ ID NO:6, such as at least 80% sequence identity with SEQ ID NO:4, SEQ ID NO:5 or SEQ ID NO:6, such as for example at least 85% sequence identity with SEQ ID NO:4, SEQ ID NO:5 or SEQ ID NO:6, such as at least 90% sequence identity with SEQ ID NO:4, SEQ ID NO:5 or SEQ ID NO:6, such as at least 95% sequence identity with SEQ ID NO:4, SEQ ID NO:5 or SEQ ID NO:6, such as for example at least 97% sequence identity with SEQ ID NO:4, SEQ ID NO:5 or SEQ ID NO:6 or such as at least 99% sequence identity with SEQ ID NO:4, SEQ ID NO:5 or SEQ ID NO:6 or part thereof.

It is preferred that the transgenic pig expresses the mutated IAPP gene. In a more preferred embodiment the transgenic pig expresses a human mutated IAPP gene. Thus, it is preferred that the transgenic pig expresses the protein encoded by the mutated IAPP gene or the human mutated IAPP gene.

The human proIAPP protein and signal peptide encoded by SEQ ID NO:1 has amino acid sequence SEQ ID NO: 7, the human proIAPP protein encoded by SEQ ID NO:2 has amino acid sequence SEQ ID NO: 8 and the human IAPP protein amylin encoded by SEQ ID NO:3 has amino acid sequence SEQ ID NO: 9.

Thus, in a preferred embodiment the transgenic pig as described herein expresses a mutated human IAPP protein having at least 80% sequence identity with SEQ ID NO: 7, SEQ ID NO: 8 or SEQ ID NO: 9 such as at least 85% sequence identity with SEQ ID NO: 7, SEQ ID NO: 8 or SEQ ID NO: 9, such as for example at least 90% sequence identity with SEQ ID NO: 7, SEQ ID NO: 8 or SEQ ID NO: 9, such as at least 95% sequence identity with SEQ ID NO: 7, SEQ ID NO: 8 or SEQ ID NO: 9, such as at least 97% sequence identity with SEQ ID NO: 7, SEQ ID NO: 8 or SEQ ID NO: 9, such as for example at least 98% sequence identity with SEQ ID NO: 7, SEQ ID NO: 8 or SEQ ID NO: 9 or such as at least 99% sequence identity with SEQ ID NO: 7, SEQ ID NO: 8, or SEQ ID NO: 9 or part thereof.

The signal peptide and mutated human IAPP protein comprising the S20G mutation as described above has amino acid sequence SEQ ID NO:10, the mutated human proIAPP protein comprising the S20G mutation has SEQ ID NO:11, whereas the mutated human amylin protein comprising the S20G mutation has SEQ ID NO:11.

Thus, in a preferred embodiment the transgenic pig as described herein expresses a mutated human IAPP protein comprising an S20G mutation and having at least 80% sequence identity with SEQ ID NO: 10, SEQ ID NO: 11 or SEQ ID NO: 12 such as at least 85% sequence identity with SEQ ID NO: 10, SEQ ID NO: 11 or SEQ ID NO: 12, such as for example at least 90% sequence identity with SEQ ID NO: 10, SEQ ID NO: 11 or SEQ ID NO: 12, such as at least 95% sequence identity with SEQ ID NO: 10, SEQ ID NO: 11 or SEQ ID NO: 12, such as at least 97% sequence identity with SEQ ID NO: 10, SEQ ID NO: 11 or SEQ ID NO: 12, such as for example at least 98% sequence identity with SEQ ID NO: 10, SEQ ID NO: 11 or SEQ ID NO: 12 or such as at least 99% sequence identity with SEQ ID NO: 10, SEQ ID NO: 11 or SEQ ID NO: 12 or part thereof.

In a specific preferred embodiment the transgenic pig expresses human IAPP protein comprising the S20G and having SEQ ID NO:10, SEQ ID NO:11 and/or SEQ ID NO:12.

In one embodiment of the present invention, the transgenic pig does not express a functional pig Islet Amyloid Polypeptide. The transgenic pig may for example comprise one or more mutations in the endogenous IAPP gene that lead to expression of a dysfunctional protein. The term 'endogenous' is used herein to specify a particular gene present naturally in the genome of a particular target cell (for example cells of a pig). In one embodiment the endogenous pig IAPP gene comprises one or more mutations that inhibit or abolish expression of the gene. In a preferred embodiment the transgenic pig does not express a pig IAPP gene. In another preferred embodiment the transgenic pig does not express an endogenous pig IAPP gene. In a specific embodiment the endogenous pig IAPP gene has been inactivated.

The mutated IAPP gene can be inserted into the porcine genome using traditional cloning techniques known by the skilled person. In one embodiment the mutated IAPP gene may be targeted to a specific region in the porcine genome by homologous recombination of a targeting construct. In a preferred embodiment a knock-in strategy is used in which the mutated IAPP gene is inserted in the genome of the pig.

Homologous recombination occurs between two homologous DNA molecules. It is also called DNA crossover. By homologous recombination, one DNA segment can replace another DNA segment with a similar sequence. The process involves breakage and reunion between the homologous regions of DNA, which is mediated by specialized enzymes such as for example site specific recombinases. The technique allows replacing one allele with an engineered construct without affecting any other locus in the genome. Using homologous recombination it is possible to direct the insertion of a transgene to a specific known locus of the host cell genome. Knowing the DNA sequence of the target locus, it is possible to replace any gene with a transgenic DNA construct, thereby either replacing or deleting the target sequence. Using this procedure, a gene can be knocked out and replaced by another gene, which is then knocked in. This procedure is known as 'gene knock-out', which allows for specific gene targeting by taking advantage of homologous recombination.

In a preferred embodiment of the present invention, the endogenous pig IAPP gene has been knocked out. Thus, a specific embodiment of the present invention relates to a transgenic pig comprising a mutated IAPP gene that has been knocked in and wherein the endogenous IAPP gene has been knocked out. In particular, it is preferred that the endogenous IAPP gene is replaced with the mutated IAPP gene (see FIG. 1).

In one embodiment a vector or DNA targeting construct comprising Transcription activator-like effector nucleases (TALEN) recognition sites is used for gene knockout and knockin (Proc Natl Acad Sci USA. 2012 Oct. 23; 109(43): 17382-7). This is exemplified in Example 1 demonstrating the use of a pIAPP-TALEN vector (SEQ ID NO:13) for knock out of the pig IAPP gene and knock in of the human IAPP gene.

In some embodiments, only one genetic modification is introduced in the genome. In other embodiments, however, the genome may be modified at more than one site. For example, the transgenic pig may comprise a mutated IAPP gene in combination with another gene mutation related to diabetes. For example, mutations in the glucose-dependent insulinotropic polypeptide (GIP) receptor and mutations in the mutant hepatocyte nuclear factor 1α (HNF1AP291fsinsC) gene are known to be associated with diabetes. Thus, in one embodiment the transgenic pig comprises a mutated IAPP gene and a mutated GIP receptor gene. In another embodiment the transgenic pig comprises a mutated IAPP gene and a mutated hepatocyte nuclear factor 1α gene. In still another embodiment the transgenic pig comprises a mutated IAPP gene and a mutated Cry1 gene (Antimorphic Cry1 Cys414Ala; PLoS ONE Vol. 8, Issue 10 (2013) e76098).

Pigs

The present invention relates to a transgenic pig comprising a mutated Islet Amyloid Polypeptide (IAPP) gene or part thereof and displaying at least one phenotype associated with diabetes. The transgenic pig of the present invention may be any pig.

The pig is genetically close to humans as compared to for example rodentia. Furthermore, the pig has been widely used in bio-medical research because of the similarities between human and porcine physiology (Douglas, 1972; Book & Bustad, 1974).

In one embodiment the transgenic pig is a wild pig. In another embodiment the transgenic pig is the domestic pig, *Sus scrofa*, such as *S. domesticus*. In yet another embodiment the invention relates to mini pigs, as well as to inbred pigs. The transgenic pig can for example be selected from the group consisting of Landrace, Yorkshire, Hampshire, Duroc, Chinese Meishan, Berkshire and Piêtrain, such as the group consisting of Landrace, Yorkshire, Hampshire and Duroc, for example the group consisting of Landrace, Duroc and Chinese Meishan, such as the group consisting of Berkshire, Pietrain, Landrace and Chinese Meishan, for example the group consisting of Landrace and Chinese Meishan. In one embodiment, the pig is not a mini-pig. In another embodiment the transgenic pig of the present invention is an inbred pig.

Due to its size and weight of about 200 kg the domestic pig is not easily handled in a laboratory setting. Thus, in a preferred embodiment of the present invention the transgenic pig is a mini-pig. The mini-pig is in one embodiment selected from the group consisting of Goettingen, Yucatan, Bama Xiang Zhu, Wuzhishan and Xi Shuang Banna. Thus, the present invention relates to any of Goettingen, Yucatan, Bama Xiang Zhu, Wuzhishan and Xi Shuang Banna separately, or in any combination. In a preferred embodiment of the invention the mini-pig is a Goettingen mini-pig.

Pigs of the present invention also include offspring of the transgenic pig comprising a mutated Islet Amyloid Polypeptide (IAPP) gene. The transgenic pig of the present invention is in one embodiment generated by cloning. The cloned pigs comprising the mutated IAPP gene can be used as breeding animals. Thus, the present invention also relates to offspring of the cloned pigs. The offspring may have different genotypes than the cloned pigs and be heterozygous with respect to the mutated IAPP gene. Thus, in one embodiment the transgenic pig is heterozygous with respect to the mutated Islet Amyloid Polypeptide (IAPP) gene. In another embodiment the transgenic pig is homozygous with respect to the mutated Islet Amyloid Polypeptide (IAPP) gene.

The present invention also relates to a transgenic blastocyst, embryo, fetus, donor cell and/or cell nucleus derived from the transgenic pig as described herein.

Further, the present invention relates to a transgenic cell or transgenic cell line from a transgenic pig of the present invention. Preferably, the transgenic cell or cell line is obtained from a germ cell and/or a somatic cell of said transgenic pig.

Phenotypes

The transgenic pig of the present invention displays at least one phenotype associated with diabetes. Thus, the transgenic pig may display any phenotype that is related to diabetes. As used herein, the term "diabetes" may be used interchangeably with "diabetes mellitus". The term "diabetes" refers to both diabetes mellitus type 1 and diabetes mellitus type 2. as well as other specific types of diabetes and gestational diabetes mellitus. A common cause of diabetes is inability of beta cells of the pancreas to produce sufficient insulin to prevent hyperglycemia. Type 1 is usually due to autoimmune destruction of the pancreatic beta cells. The hallmark of type 2 is tissue-wide insulin resistance. Initially, the pancreatic beta cells will attempt to compensate for the insulin resistance by increased insulin production. As a result, due to the exhausting insulin producing activity, type 2 diabetes mellitus, sometimes progresses to loss of beta cell function as well. Gestational diabetes is similar to type 2 diabetes mellitus, in that it involves insulin resistance. In gestational diabetes, the hormones of pregnancy cause insulin resistance in those women genetically predisposed to developing this condition.

Insulin resistance and type 2 diabetes is associated with a number of serious clinical conditions. Conditions associated with insulin resistance and/or diabetes include atherosclerosis, arteriosclerosis, arteriolosclerosis, hypertension, cardiovascular disorders, type 2 diabetes mellitus, retinopathy, neuropathy, nephropathy, microangiopathy, macroangiopathy, hyperglycemia, hypercholesterolemia, hyperinsulinemia, hyperlipidemia, overweight, visceral obesity, dyslipidemia, insulin resistance, impaired oral glucose tolerance, impaired fasting glucose, metabolic syndrome, polycystic ovary syndrome, fatty liver (steatosis hepatis), ischemia, ischemic heart disease, thrombotic stroke, haemorrhagic stroke, limb ischemia, and/or claudication. Each of the disorders or conditions specified above is intended to be an individual embodiment.

Type 2 diabetes and insulin resistance is also associated with an increased incidence of metabolic syndrome. Metabolic syndrome is a cluster of metabolic risk factors in an individual. These risk factors include overweight/obesity, hypertension/cardiovascular disorders, type 2 diabetes mellitus, and dyslipidemia. Thus, the term "metabolic syndrome" according to the present invention is meant to comprise those risk factors. Metabolic syndrome is also sometimes referred to as metabolic syndrome X, syndrome X, insulin resistance syndrome, Reaven's syndrome or CHAOS. As is apparent from above, the individual risk factors involved in metabolic syndrome may also constitute an individual clinical condition associated with type 2 diabetes In one embodiment the transgenic pig displays at least one phenotype associated with type 2 diabetes. In another embodiment the transgenic pig displays at least one phenotype associated with type 1 diabetes.

In one embodiment the transgenic pig has diabetes. In a more specific embodiment thereof the transgenic pig has type 1 diabetes. In yet another embodiment the transgenic pig has type 2 diabetes.

In general, symptoms or phenotypes of untreated diabetes include weight loss, polyuria (frequent urination), polydipsia (increased thirst), and polyphagia (increased hunger). Thus, in one embodiment the transgenic pig display at least one phenotype selected from the group consisting of weight loss, polyuria and polyphagia.

Primary microvascular complications of diabetes include damage to the eyes, kidneys, and nerves. Damage to the eyes, known as diabetic retinopathy, is caused by damage to the blood vessels in the retina of the eye, and can result in gradual vision loss and potentially blindness. Damage to the kidneys, known as diabetic nephropathy, can lead to tissue scarring, urine protein loss, and eventually chronic kidney disease, sometimes requiring dialysis or kidney transplant. Damage to the nerves of the body, known as diabetic neuropathy, is the most common complication of diabetes. The symptoms can include numbness, tingling, pain, and altered pain sensation, which can lead to damage to the skin. Diabetes-related foot problems (such as diabetic foot ulcers) may occur, and can be difficult to treat, occasionally requiring amputation. Additionally, proximal diabetic neuropathy causes painful muscle wasting and weakness.

Thus, in another embodiment the transgenic pig displays at least one phenotype selected from the group consisting of eye damage, diabetic nephropathy, diabetic neuropathy, urine protein loss, damage to the skin, diabetic foot ulcers and muscle wasting.

In a preferred embodiment the transgenic pig displays at least one phenotype selected from the group consisting of blindness, inflammation, infection and organ deformation.

Degeneration of the β-cells is the main cause of type I diabetes mellitus. Also, the clinical course of type 2 diabetes is characterized by a progressive decline in β-cell mass and function. The β-cells constitute the predominant type of cells in the islets of the pancreas and they are responsible for the secretion of insulin. Therefore, β-cell degeneration is associated with a decline in the secretion of insulin.

In another preferred embodiment of the present invention the at least one phenotype displayed by the transgenic pig is beta cell degeneration. β-cell degeneration can for example be determined by assessing the beta cell mass in a pancreatic tissue sample.

In a preferred embodiment the at least one phenotype displayed by the transgenic pig is glucose intolerance or hyperglycemia. Glucose intolerance is an umbrella term for metabolic conditions which result in higher than normal blood glucose levels—hyperglycemia. Hyperglycemia as used herein is a condition in which an excessive amount of glucose circulates in the blood plasma.

Glucose intolerance includes anyone with either impaired fasting glucose (IFG) or impaired glucose tolerance (IGT).

Phenotypes associated with diabetes can also be detected as abnormal levels of glucose, glucagon, insulin and/or the c-peptide of the transgenic pig.

Insulin is the principal hormone that regulates the uptake of glucose from the blood into most cells of the body, especially liver, muscle, and adipose tissue. Therefore, deficiency of insulin or the insensitivity of its receptors plays a central role in all forms of diabetes. Insulin plays a critical role in balancing glucose levels in the body. Insulin can inhibit the breakdown of glycogen or the process of gluconeogenesis, it can stimulate the transport of glucose into fat and muscle cells, and it can stimulate the storage of glucose in the form of glycogen. C-peptide, which is also known as connecting peptide, connects insulin's A-chain to its B-chain in the proinsulin molecule. C-peptide is secreted along with insulin and is normally secreted in equimolar amounts to insulin.

Insulin is released into the blood by β-cells, found in the islets of Langerhans in the pancreas, in response to rising levels of blood glucose, typically after eating. Insulin is used by about two-thirds of the body's cells to absorb glucose from the blood for use as fuel, for conversion to other needed molecules, or for storage. Lower glucose levels result in decreased insulin release from the β-cells and in the breakdown of glycogen to glucose. This process is mainly controlled by the hormone glucagon, which acts in the opposite manner to insulin.

If the amount of insulin available is insufficient, if cells respond poorly to the effects of insulin (insulin insensitivity or insulin resistance), or if the insulin itself is defective, then glucose will not be absorbed properly by the body cells that require it, and it will not be stored appropriately in the liver and muscles. The net effect is persistently high levels of blood glucose, poor protein synthesis, and other metabolic derangements Thus, high glucose levels, high glucagon levels, low insulin levels and/or low c-peptide levels are normally associated with diabetes.

The glucose level, glucagon level, insulin level and/or the c-peptide level can for example be determined by measuring the concentration of glucose, glucagon, insulin and/or c-peptide in a urine sample or a blood or plasma sample from the pig. The obtained values, i.e. the measured levels of glucose, glucagon, insulin and/or c-peptide are in a preferred embodiment compared with the levels of glucose, glucagon, insulin and/or c-peptide in a control pig. It is preferred that the control pig does not comprise a mutated IAPP gene. In a preferred embodiment the control pig is a wild type pig. It is appreciated that the control pig is of the same race as the transgenic pig.

In one embodiment the transgenic pig display higher glucose levels, higher glucagon levels, lower insulin levels and/or lower c-peptide levels when compared to a control pig.

Thus, in a preferred embodiment the transgenic pig display higher glucose levels when compared to a control pig. The term "glucose level" as used herein refers to the blood glucose level or the plasma glucose level of the pig. Thus, the glucose level is the concentration of glucose in the blood or in the plasma of the pig. The glucose level of the pigs depends on the diet given to the pigs. Pigs given a normal diet will for example display higher glucose levels than fasting pigs.

Thus, in one embodiment the transgenic pig displays higher glucose levels when compared to a control pig and wherein said transgenic pig and said control pig are given a normal diet. It is preferred that the transgenic pig and the control pig are given the same diet and that the blood glucose levels are measured at the same time points after a meal.

In one embodiment the glucose level of the transgenic pig is increased by at least 5%, such as for example at least 15%, such as at least 20%, such as for example at least 30%, at least 40%, such as at least 50%, such as for example at least 60%, such as at least 70%, such as for example at least 80% or such as at least 100% when compared to a control pig and wherein said transgenic pig and said control pig are given a normal diet.

In a preferred embodiment the glucose level of the transgenic pig is increased by at least 10% when compared to a control pig and wherein said transgenic pig and said control pig are given a normal diet.

In yet another preferred embodiment of the present invention the transgenic pig as described herein display higher glucagon levels when compared to a control pig. The term "glucagon level" as used herein refers to the blood glucagon level or the plasma glucagon level of the pig. Thus, the glucagon level is the concentration of glucagon in the blood or in the plasma of the pig. The glucagon level of the pigs depends on the diet given to the pigs. Pigs given a normal diet will for example display higher glucagon levels than fasting pigs.

Thus, in one embodiment the transgenic pig display higher glucagon levels when compared to a control pig and wherein said transgenic pig and said control pig are given a normal diet.

In one embodiment the glucagon level of the transgenic pig is increased by at least 5%, such as for example at least 15%, such as at least 20%, such as for example at least 30%, at least 40%, such as at least 50%, such as for example at least 60%, such as at least 70%, such as for example at least 80% or such as at least 100% when compared to a control pig and wherein said transgenic pig and said control pig are given a normal diet.

In a preferred embodiment the glucagon level of the transgenic pig is increased by at least 10% when compared to a control pig and wherein said transgenic pig and said control pig are given a normal diet.

In another preferred embodiment of the present invention the transgenic pig as described herein display lower insulin levels when compared to a control pig. The term "insulin level" as used herein refers to the insulin concentration in the blood or plasma of the pig. The insulin level of the pigs depends on the diet given to the pigs. Pigs given a normal diet will for example display higher insulin levels than pigs under a fasting diet (see FIG. 4C).

Thus, in one embodiment the transgenic pig display lower insulin levels when compared to a control pig and wherein said transgenic pig and said control pig are given a normal diet.

In one embodiment the insulin level of the transgenic pig is decreased by at least 5%, such as for example at least 15%, such as at least 20%, such as for example at least 30%, at least 40%, such as at least 50%, such as for example at least 60%, such as at least 70%, such as for example at least 80% or such as at least 100% when compared to a control pig and wherein said transgenic pig and said control pig are given a normal diet.

In a preferred embodiment the insulin level of the transgenic pig is decreased by at least 10% when compared to a control pig and wherein said transgenic pig and said control pig are given a normal diet.

In another preferred embodiment of the present invention the transgenic pig as described herein display lower c-peptide levels when compared to a control pig. The term "c-peptide level" as used herein refers to the c-peptide concentration in the blood or plasma of the pig. The c-peptide level of the pigs depends on the diet given to the pigs. Pigs given a normal diet will for example display higher c-peptide levels than fasting pigs.

Thus, in one embodiment the transgenic pig display lower c-peptide levels when compared to a control pig and wherein said transgenic pig and said control pig are given a normal diet.

In one embodiment the c-peptide level of the transgenic pig is decreased by at least 5%, such as for example at least 15%, such as at least 20%, such as for example at least 30%, at least 40%, such as at least 50%, such as for example at least 60%, such as at least 70%, such as for example at least 80% or such as at least 100% when compared to a control pig and wherein said transgenic pig and said control pig are given a normal diet.

In a preferred embodiment the c-peptide level of the transgenic pig is decreased by at least 10% when compared to a control pig and wherein said transgenic pig and said control pig are given a normal diet.

It is preferred that the transgenic pigs and the control pigs are given the same diet and that the blood glucose levels, insulin levels, c-peptide levels and/or glucagon levels are measured at the same time points after a meal. In a preferred embodiment the transgenic pig and the control pig have the same age.

Method for Producing the Transgenic Pig

The transgenic pig of the present invention may be produced using any technique in which modified genetic material is transferred from a donor cell to a host cell, such as an enucleated oocyte. A number of techniques exist such as introducing genetic material from a transgenic somatic cell into an enucleated oocyte by for example microinjection or by nuclear transfer.

In one embodiment of the present invention the transgenic pig is obtainable by somatic cell nuclear transfer. Somatic cell nuclear transfer refers to the transfer of the nucleus of a somatic (body) cell or somatic cell into an egg cell (oocyte) which has had its own nucleus removed (denucleated or enucleated).

Thus, another aspect of the present invention relates to a method for producing the transgenic pig as described herein, said method comprising:
  i. producing an oocyte having a partially modified zona pellucida
  ii. separating the oocyte into at least two parts obtaining an oocyte having a nucleus and at least one cytoplast
  iii. producing a donor cell comprising a mutated IAPP gene or part thereof
  iv. fusing at least one cytoplast with the donor cell or membrane surrounded cell nucleus
  v. obtaining a reconstructed embryo,
  vi. activating the reconstructed embryo to form an embryo, culturing said embryo and
  vii. transferring said cultured embryo to a host mammal, wherein the embryo develops into a transgenic pig.

It is appreciated that the methods for producing the transgenic pig as described herein do not encompass a surgical step performed on the pig.

The mutated IAPP gene is as defined elsewhere herein. Thus, in a preferred embodiment the mutated IAPP gene is a human mutated IAPP gene. In a preferred embodiment thereof the human mutated IAPP gene comprises an S20G mutation.

In a preferred embodiment the donor cell does not express a pig IAPP gene. In another preferred embodiment the donor cell does not express an endogenous pig IAPP gene. In another preferred embodiment the pig IAPP gene has been knocked out.

The oocyte of ii) may in another embodiment be separated into at least three parts obtaining at least two cytoplasts. In one embodiment the oocyte is separated into two parts obtaining one cytoplast. In another embodiment the oocyte is separated into three parts obtaining two cytoplasts.

Oocyte

The term 'oocyte' according to the present invention means an immature female reproductive cell, one that has not completed the maturing process to form an ovum (gamete). In the present invention an enucleated oocyte is the recipient cell in the nuclear transfer process.

The oocytes according to the present invention are isolated from oviducts and/or ovaries of a pig. Normally, oocytes are retrieved from deceased pigs, although they may be isolated also from either oviducts and/or ovaries of live pigs. In one embodiment the oocytes are isolated by oviductal recovery procedures or transvaginal recovery methods. In a preferred embodiment the oocytes are isolated by aspiration. Oocytes are typically matured in a variety of media known to a person skilled in the art prior to enucleation. The oocytes can also be isolated from the ovaries of a recently sacrificed animal or when the ovary has been frozen and/or thawed. Preferably, the oocytes are freshly isolated from the oviducts.

Oocytes or cytoplasts may also be cryopreserved before use. While it will be appreciated by those skilled in the art that freshly isolated and matured oocytes are preferred, it will also be appreciated that it is possible to cryopreserve the oocytes after harvesting or after maturation. If cryopreserved oocytes are utilised then these must be initially thawed before placing the oocytes in maturation medium. Methods of thawing cryopreserved materials such that they are active after the thawing process are well-known to those of ordinary skill in the art. However, in general, cryopreservation of oocytes and cytoplasts is a very demanding procedure, and it is especially difficult in pigs, because of the above mentioned general fragility of pig oocytes and cytoplasts, and because of the high lipid content that makes them very sensitive to chilling injury (i.e. injury that occurs between +15 and +5° C. during the cooling and warming procedure).

In another embodiment, mature (metaphase II) oocytes that have been matured in vivo, may be harvested and used in the nuclear transfer methods disclosed herein. Essentially, mature metaphase II oocytes are collected surgically from either nonsuperovulated or superovulated pigs 35 to 48 hours past the onset of estrus or past the injection of human chorionic gonadotropin (hCG) or similar hormone.

Where oocytes have been cultured in vitro, cumulus cells that are surrounding the oocytes in vivo may have accumulated may be removed to provide oocytes that are at a more suitable stage of maturation for enucleation. Cumulus cells may be removed by pipetting or vortexing, for example, in the presence of in the range of 0.1 to 5% hyaluronidase, such as in the range of 0.2 to 5% hyaluronidase, for example in the range of 0.5 to 5% hyaluronidase, such as in the range of 0.2 to 3% hyaluronidase, for example in the range of 0.5 to 3% hyaluronidase, such as in the range of 0.5 to 2% hyaluronidase, for example in the range of 0.5 to 1% hyaluronidase, such as 0.5% hyaluronidase.

The first step in the preferred methods involves the isolation of a recipient oocyte from a suitable pig. In this regard, the oocyte may be obtained from any pig source and at any stage of maturation.

The stage of maturation of the oocyte at enucleation and nuclear transfer has been reported to be of significance for the success of nuclear transfer methods. Immature (prophase I) oocytes from pig ovaries are often harvested by aspiration. In order to employ techniques such as genetic engineering, nuclear transfer and cloning, such harvested oocytes are preferably matured in vitro before the oocyte cells may be used as recipient cells for nuclear transfer.

Preferably, successful pig embryo cloning uses the metaphase II stage oocyte as the recipient oocyte because it is believed that at this stage of maturation the oocyte can be or is sufficiently activated to treat the introduced nucleus as if it were a fertilising sperm. However, the present invention relates to any maturation stage of the oocyte which is suitable for carrying out somatic cell nuclear transfer, embryos, blastocysts, and/or transgenic pigs obtainable by the method of somatic cell nuclear transfer of the present invention.

The in vitro maturation of oocytes usually takes place in a maturation medium until the oocyte has reached the metaphase II stage or has extruded the first polar body. The time it takes for an immature oocyte to reach maturation is called the maturation period.

In a preferred embodiment of the present invention the oocyte is from sow or gilt, preferably from a sow.

The donor (somatic cell or nucleus of somatic cell) and recipient (cytoplast) involved in the cell nuclear transfer method according to the present invention is a pig. Likewise, reconstructed embryos may be implanted in a pig according to the present invention. The different pigs suitable as donor, recipient or foster mother are described elsewhere herein.

The donor pig according to the present invention may be female, or male. The age of the pig can be any age such as an adult, or for example a fetus.

Embryo

According to the present invention a reconstructed embryo (i.e. single cell embryo) contains the genetic material of the donor cell. Subsequently, the reconstructed embryo divides progressively into a multi-cell embryo after the onset of mitosis. In vitro the onset of mitosis is typically induced by activation as described herein.

In the present invention the term 'embryo' also refers to reconstructed embryos which are embryos formed after the process of nuclear transfer after the onset of mitosis by activation. Reconstructed embryos are cultured in vitro.

When the embryo contains about 12-16 cells, it is called a "morula". Subsequently, the embryo divides further and many cells are formed, and a fluid-filled cystic cavity within its center, blastocoele cavity. At this stage, the embryo is called a "blastocyst". The developmental stage of the "fertilized" oocyte at the time it is ready to implant; formed from the morula and consists of an inner cell mass, an internal cavity, and an outer layer of cells called trophectodermal cells.

The blastocyst according to the present invention may be implanted into the uterus of a host mammal, in particular a pig, preferably a Goettingen minipig and continues to grow into a fetus and then an animal.

In the methods provided herein for producing transgenic or transgenic non-human mammal, for cloning a non-human mammal, for culturing a reconstructed embryo, and/or for cryopreservation of a pig embryo, the embryo may be cultured in vitro. The embryo may for example be cultured in sequential culture. It will be appreciated that the embryo may be a normal embryo or a reconstructed embryo as defined elsewhere herein.

Cytoplast

A cytoplast is an oocyte or a part of an oocyte from which the nucleus has been removed. In a preferred method of the invention, the nucleus of an oocyte is replaced with a donor cell, which comprises a mutated IAPP gene as defined elsewhere herein.

Donor Cell

By the term 'donor cell' of the present invention is meant somatic cell and/or cells derived from the germ line. The donor cell comprises a mutated IAPP gene. The mutated IAPP gene of the donor cell is as defined elsewhere herein.

By the term 'somatic cell' of the present invention is meant any (body) cell from an animal at any stage of development. For example somatic cells may originate from fetal, neonatal or adult tissue. Especially preferred somatic cells are those of foetal or neonatal origin. However, cells from a germ line may also be used. According to the present invention a donor cell is a somatic cell. In another embodiment of the present invention the donor cell is a cell derived from a germ cell line.

Somatic cells are in one embodiment selected from the group consisting of epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells. In a preferred embodiment the donor cell is a fibroblast cell.

These may be obtained from different organs, e.g., skin, lung, pancreas, liver, stomach, intestine, heart, reproductive organs, bladder, kidney, urethra and other urinary organs.

The pigs from which the somatic cells may be derived are described elsewhere herein. A preferred embodiment of the invention is the use of somatic cells originating from the same species as the recipient oocyte (cytoplast).

Preferably, the somatic cells are fibroblast cells. The fibroblast can be obtained from fetuses, newborn piglets and adult animals. Fibroblasts may furthermore be easily propagated in vitro. Most preferably, the somatic cells are in vitro cultured fibroblasts of foetal or neonatal origin.

In a preferred embodiment the somatic cells are modified. In yet a further preferred embodiment of the present invention the somatic cells are preferably of foetal or neonatal origin, or for example from adults.

One aspect of the present invention relates to a modified donor cell and/or cell nucleus derived from the modified pig model as disclosed herein and/or a modified donor cell and/or cell nucleus comprising a mutated IAPP gene. It is appreciated that the modified donor cell may be any type of tissue as described elsewhere herein.

The donor cells may be transgenic by any of standard method known in the art. The genetic modification may be a modification of the genomic DNA by deletion, insertion, duplication and/or other forms of mutation, including point mutation. The modification may be made in coding sequences and/or non-coding sequences.

In the present invention a mutated IAPP gene is inserted into the genome of the donor cell. Thus, DNA constructs for insertion comprises a mutated IAPP gene. The IAPP gene is as described elsewhere herein.

Suitable techniques for genetic modification of mammalian cells, such as fibroblasts, include techniques such as gene addition by nonhomologous recombination, gene replacement by homologous recombination, and gene editing. This may include the use of retroviral insertion, transposon transfer and/or artificial chromosome techniques. Nonhomologous DNA recombination may e.g. be carried out as described in Kragh et al. (2004) Reprod. Fert. Dev. 16:290 or Kragh et al. (2004) Reprod. Fert. Dev. 16:315, Transposon-based gene transfer may be carried out as described in Izsvak et al. (1997) Cell 91:501. Gene replacement by homologous recombination may e.g. involve the techniques described by Urnow et al. (2005) Nature 435: 646. Techniques for gene editing have been described in Andersen et al. (2002) J. Mol. Med. 80:770, Liu et al (2002) Gene Ther. 9:118 and Sorensen et al. (2005) J. Mol. Med. 83:39.

In a preferred embodiment the donor cell is transgenic by random integration of the genes disclosed herein into the genome of the donor cell.

Use of the Transgenic Pig

The transgenic pigs according to the present invention constitute a highly suitable model system for diabetes mellitus because, as described herein, they exhibit key features of diabetes such as for example impaired insulin secretion and high blood glucose levels.

Therefore, another aspect of the present invention relates to use of the transgenic pig as described herein for study of diabetes such as diabetes mellitus type 1 or diabetes mellitus type 2.

The study of diabetes may involve determining the beta cell mass, insulin level, c-peptide level, glucose level and/or glucagon level of said pig. The beta cell mass, insulin level, c-peptide level, glucose level and/or glucagon level of said pig may be determined at different ages of the pig, such as for example at an age of 1 week, 2 weeks, 3 weeks, 4 weeks, 1 month, 2 months, 3 months, 6 months and/or 1 year. The beta cell mass, insulin level, c-peptide level, glucose level and/or glucagon level of said pig may be determined at different time points such as for example daily, twice a week, weekly, every second week, monthly or every second month.

Thus, the transgenic pig of the present invention can be used as a model system for the pathogenesis of diabetes mellitus and for studying the onset, development and progress of diabetes.

The transgenic pig of the present invention may also be used as a model for studying treatments and/or prevention of diabetes. Thus, a further aspect of the present invention relates to use of the transgenic pig as a model system for studying therapy, treatment and/or prevention of diabetes. Hereby, the pigs can be used for identifying means and methods suitable for the therapy, treatment or prevention of diabetes.

The pigs can also be used for identifying compounds suitable for the therapy, treatment and/or prevention of diabetes. Such a method preferably comprises the following steps (i) providing a transgenic pig according to the present invention,
(ii) providing a compound to be tested,
(iii) administering said compound to said transgenic pig,
(iv) determining risk factors associated with diabetes, such as the insulin level, glucose level and/or glucagon level of said transgenic pig, thereby determining the effect of said compound on the insulin level, glucose level, glucagon level and/or c-peptide level of said transgenic pig.

The insulin level, glucose level and/or glucagon level can be determined as described elsewhere herein.

Preferably, such a compound is able to improve insulin secretion and/or decrease glucose and glucagon levels.

Preferred administration routes of a compound are oral, nasal, subcutaneous, intracutaneous, parenteral, transdermal, topical, intravenous, intraarterial, intramuscular, intraperitoneal or combinations thereof.

A promising method for treating diabetes or diabetes millitus type I, involves whole pancreas or islet cell transplantation, wherein β-cells are removed from a donor's pancreas and transferred into an individual with diabetes. Once transplanted, the donor islets begin to make and release insulin.

The transgenic pig of the present invention can also be used as a model for studying transplantation of β-cells. Thus, a further embodiment of the present invention relates to use of the transgenic pig as a model system for the therapy, treatment and/or prevention of diabetes, wherein said therapy or treatment involves transplantation of β-cells from a donor pig to said transgenic pig.

β-cells can be isolated from donor pancreas and subsequently transplanted into the transgenic pig.

A further aspect of the present invention relates to a method for study of diabetes by applying the transgenic pig as described herein.

Another aspect relates to a method for studying therapy, treatment and/or prevention of diabetes comprising the steps of i. providing a transgenic pig according to any of claims 1 to 16
ii. providing a compound to be tested,
iii. administering said compound to said transgenic pig,
iv. determining risk factors associated with diabetes, such as the insulin level, glucose level and/or glucagon level of said transgenic pig, thereby determining the effect of said compound on the insulin level, glucose level, glucagon level and/or c-peptide level of said transgenic pig.

EXAMPLES

Materials and Methods
Cells

Primary porcine fibroblasts from Göttingen minipigs were used for gene targeting. Cells were cultured in DMEM supplemented with 15% FBS, 1/100 P/S, 1/100 glutamine. Human FGF (5 ng/ml) was supplemented when cells were in the selection medium (G418, 1 μg/ml).
Constructs The HIP pig targeting construct and TALENs illustrated in FIG. 1 were generated by PCR and golden-gate assembling. TALEN targeted sequences are provided in table 1.
Transfection and Selection All transfections were performed with Nucleofection X unit. Three days after transfection (2 days after splitting into 96-well plates), cells were selected with G418 (1 mg/ml) for 2 weeks with the medium changed every 3-4 days. After selection, G418-resistant cell clones were trypsinized, and ⅓ were transferred to 96-well PCR plates for PCR screening; ⅓ were cultured in gelatin-coated 96-well cell culture plates for Southern blot analysis; ⅓ were cultured in gelatin-coated 96-well plates for freezing and these cells were subsequently used as nuclear donor cells for Somatic cell nuclear transfer (SCNT).
Oocyte Collection and In Vitro Maturation Except where otherwise indicated all chemicals for the embryological work were obtained from Sigma-Aldrich Co. (St Louis, Mo., USA). Cumulus-oocyte complexes (COC) were aspirated from 2 to 6 mm follicles from slaughterhouse-derived sow ovaries and matured in groups of 50 in 400 II in vitro maturation (IVM) medium consisting of bicarbonate-buffered TCM-199 (GIBCO BRL, USA) supplemented with 10% (v/v) cattle serum (CS), 10% (v/v) pig follicular fluid, 10 IU/ml equine chorionic gonadotrophin, and 5 IU/ml human chorionic gonadotrophin (Suigonan Vet; Skovlunde, Denmark) in the Submarine Incubation System (SIS) for 41-44 h.
Handmade Cloning and Embryo Culture COCs were shortly treated with 1 mg/ml hyaluronidase and pipetted vigorously to remove the cumulus cells attached to the zonae pellucidae. Zonae pellucidae of oocytes were partially digested with 3.3 mg/ml pronase solution dissolved in T33 (T for Hepes buffered TCM199, GIBCO BRL, USA; while the number refers to the concentration of CS, here 33%) for 20 s, followed by quick washing in T2 and T20 drops. Oocytes with distended and softened zonae pellucidae were lined up in T2 drops supplemented with 2.5 μg/ml cytochalasin B. With a finely drawn and fire-polished glass pipette, oocytes were rotated to locate the polar body. Oriented bisection was performed manually with ultra-sharp splitting blades (AB Technology, Pullman, Wash., USA) under a stereomicroscope. Less than half of the cytoplasm close to the polar body was removed from the remaining putative cytoplast. Fibroblasts (5D1) were trypsinized and re-suspended in 20 μl of T2. Fusion was performed in two steps, where the second one included the initiation of activation. For the first step, 50% of the available cytoplasts were transferred into 1 mg/ml of phytohaemagglutinin (PHA; ICN Pharmaceuticals, Girraween, Australia) dissolved in TO for 3 s, and then each one was quickly dropped over a single fibroblast cell. After attachment, cytoplast-fibroblast pairs were equilibrated in fusion medium (0.3 M mannitol and 0.01% polyvinyl alcohol; PVA) for 10 s and transferred to a fusion chamber (BTX microslide 0.5 mm fusion chamber, model 450; BTX, San Diego, Calif., USA). Using AC of 0.06 kV/cm and 700 kHz, pairs were aligned to the wire of the fusion chamber with the somatic cells farthest from the wire, then fused with a DC pulse of 2.0 kV/cm for 9 μs. After the DC pulse, pairs were removed carefully from the wire, transferred to T10 drops and incubated further to observe whether fusion had occurred. Approximately 1 h after the first fusion, each pair was fused with another cytoplast in activation medium (0.3 M mannitol, 0.1 mM $MgSO_4$, 0.5 mM $CaCl_2$ and 0.1% PVA). By using an AC of 0.06 kV/cm and 700 kHz, one fused pair and one cytoplast were aligned to one wire of the fusion chamber, with fused pairs contacting the wire. A single DC pulse of 0.86 kV/cm was applied for 80 μs. When fusion had been observed in T10 drops, reconstructed embryos were transferred into PZM-3 supplemented with 5 μg/ml cytochalasin B and 10 μg/ml cycloheximide. After a 4 h incubation at 38.5° C. in 5% $CO_2$, 5% $O_2$ and 90% $N_2$ with maximum humidity, embryos were washed three times and cultured in PZM-3 (Yoshioka K et al., (2002), Biol Reprod 66:112-119) using the well of the well system (Vajta G et al., (2000), Mol Reprod Dev 55:256-264).
Embryo Transfer D5 and D6 fresh blastocysts were surgically transferred into both uterine horns of Danish Landrace sows on day 4 after weaning. Pregnancy was diagnosed by ultrasonography on day 21 and confirmed every second week. The farrowing was induced with an injection of prostaglandine if the sow did not show signs of labor as late as day 121. All animals were housed and cared for in strict accordance to the proposals for animal research reviewed by the Danish Institute of Agricultural Sciences and the Danish Centre for Bioethics and Risk Assessment. Experimental permission was given by the Danish Animal Ethics Committee.

Example 1: Generation of the HIP Pigs

Figure 2:
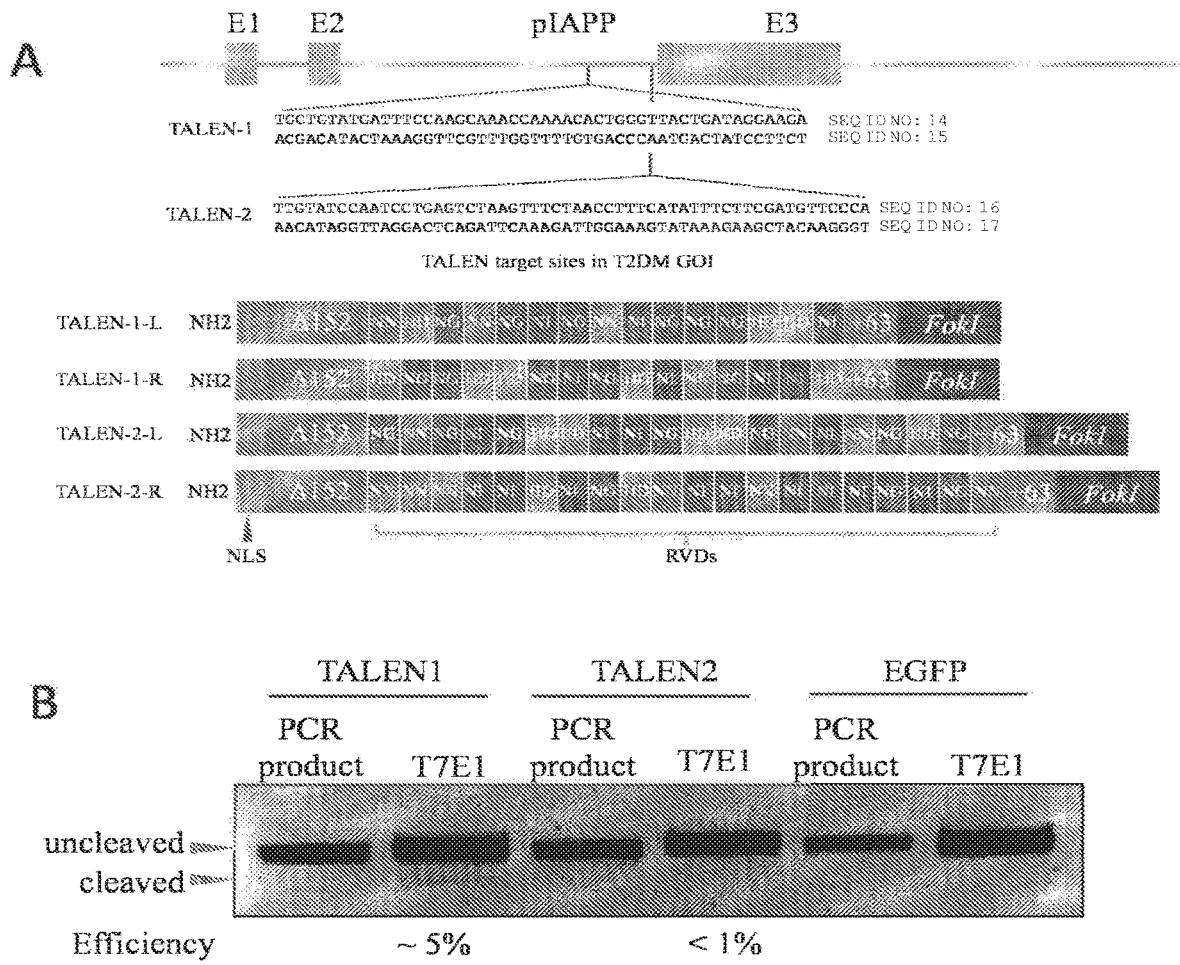
FIG. 2. Generation and validation of pIAPP TALENs. (A) Illustration of the two pairs of pIAPP TALENs, TALEN-1 (SEQ ID NO:14 and SEQ ID NO:15) and TALEN-2 (SEQ ID NO:16 and SEQ ID NO:17). (B) T7E1 based assay of TALEN mediated cleaving efficiency. The first TALEN pair (TALEN1) has the highest efficiency, about 5%, and was selected for gene targeting.

The human IAPP pigs (HIP pigs) comprise a mutated IAAP gene comprising the mutation S20G as described elsewhere herein. A HIP pig targeting construct (SEQ ID NO: 13) as illustrated in FIG. 1 was generated. The strategy combines complete pIAPP knockout with targeted hIAPP knockin (pIAPPKO; hIAPPKI) using pIAPP-TALENs together with the targeting construct. A pair of TALENs with cleaving efficiency of approximately 5%, measured by T7E1 assay (FIG. 2), created DNA double strand breaks in intron 2 of the pIAPP gene to enhance the targeting efficiency by homologous recombination (HR). The targeting construct was designed in a way that allows, upon homologous recombination, the endogenous pIAPP gene to be replaced by a transgene, in which the expression of hIAPP is regulated by the rat insulin 2 promoter (RIP2). The transgene also carries an antibiotic selection cassette which, after use, can be removed by Cre recombinase.

We transfected porcine primary fibroblasts (Göttingen minipigs) with the targeting construct and the pIAPP-TALEN vectors. Targeted cell clones were found by PCR-screening of cell clones selected due to antibiotic (Geneticin, G418) resistance. 24 single-cell clones, which are pIAPP-KO;hIAPPKI, were selected and pooled. The pooled cells were used as nuclear donors for generating the cloned pigs by HMC.

Figure 3:
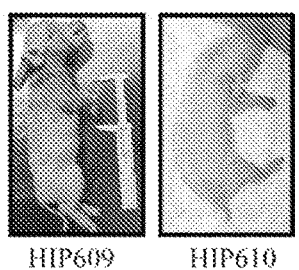
FIG. 3 Generation of HIP pigs by HMC (HandMade Cloning). (a) Three HMC transfers were conducted. A total of five HIP pigs (3 still born and 2 liveborn) were obtained out of a total of 233 embryos. (b) Photo of HIP pig 609 and 610. (c) Birth weight of the HIP pigs. (d) Growth rate of the HIP 609 and HIP 610. (e & f) Genotyping of the HIP pigs by PCR and Southern blotting. Primers and Southern blot probes are indicated in the illustrated figure. HIP 609 was found to be a knockout in one allele and a knockin with the human IAPP in the other allele.
Figure 3:
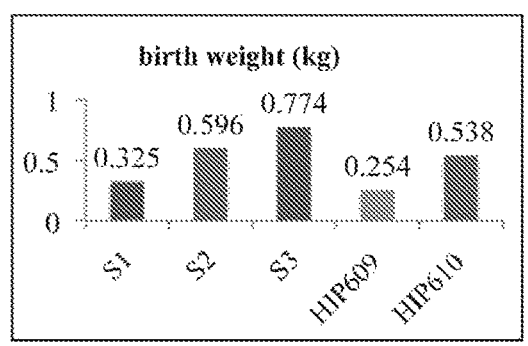
Figure 3:
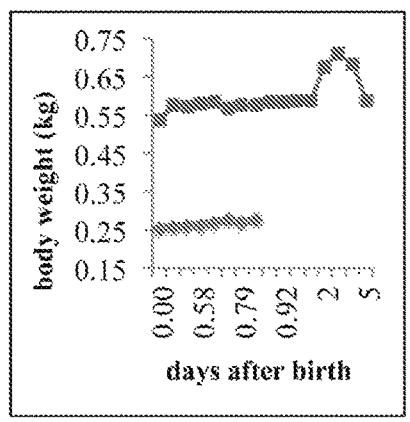

In the first round of HMC, a total of 5 HIP pigs were generated, 2 liveborn and 3 stillbone ones out of three transfers. One of the liveborn HIP pig was confirmed to be deficient of the endogenous porcine IAPP genes and to carry one copy of the human IAPP(S20G) gene (HIP pig 609 in FIG. 3). Fibroblasts from this HIP pig 609 were used as nuclear donor cells to generate more HIP pigs (a procedure called recloning). A total of 27 liveborn HIP pigs with the correct genotype were generated out of five transfers.

Example 2: Characterization and Validation of T2DM in the HIP Pigs

Figure 4:
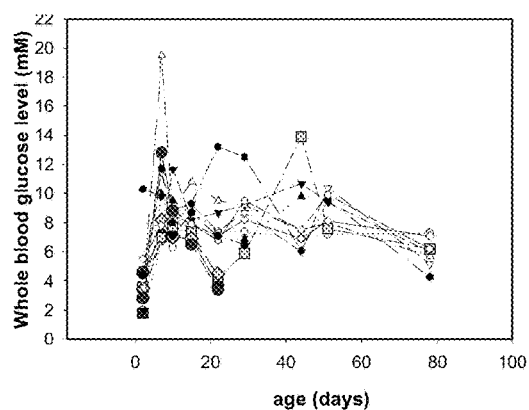
FIG. 4. Time-course of whole blood glucose and body weight measurements in some of the HIP pigs. (A) Whole blood glucose measurement for three months. (B) Body weight measurement for the first three month. (C) Fasting and none-fasting blood glucose measurement in 44 days old HIP pigs. Glucose was detected in urine samples of two HIP pigs (HIP 543 and HIP 544).
Figure 4:
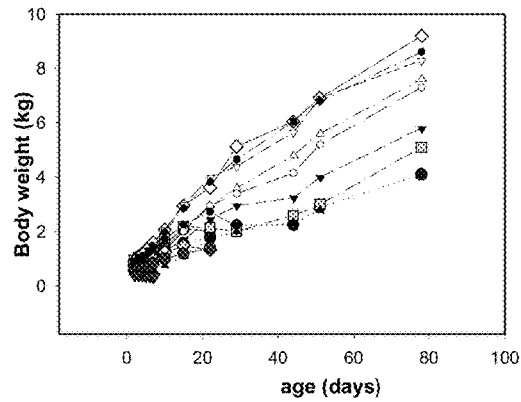
Figure 4:
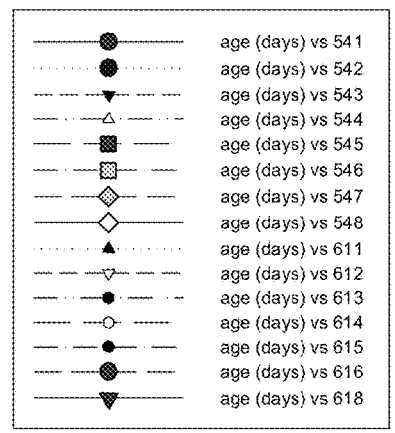
Figure 4:
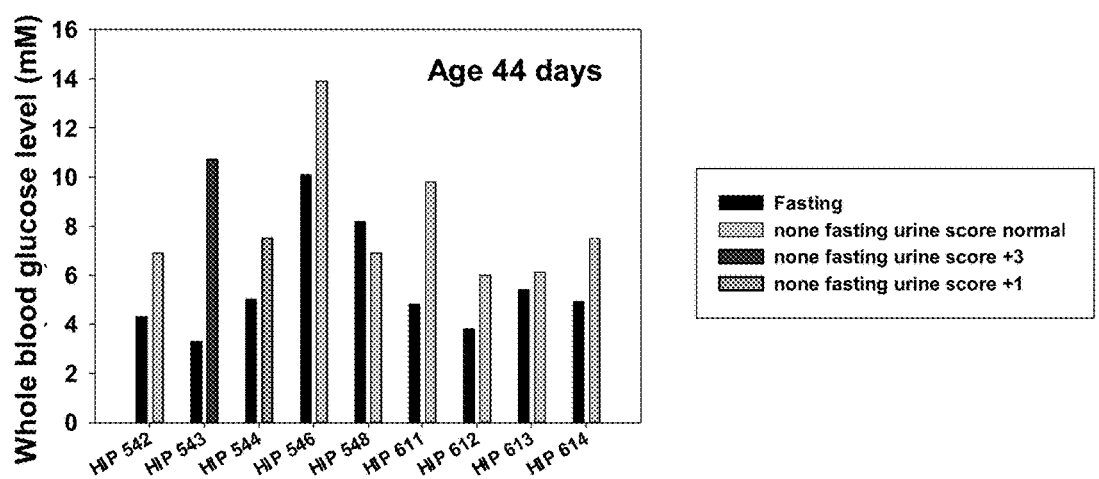
Figure 5:
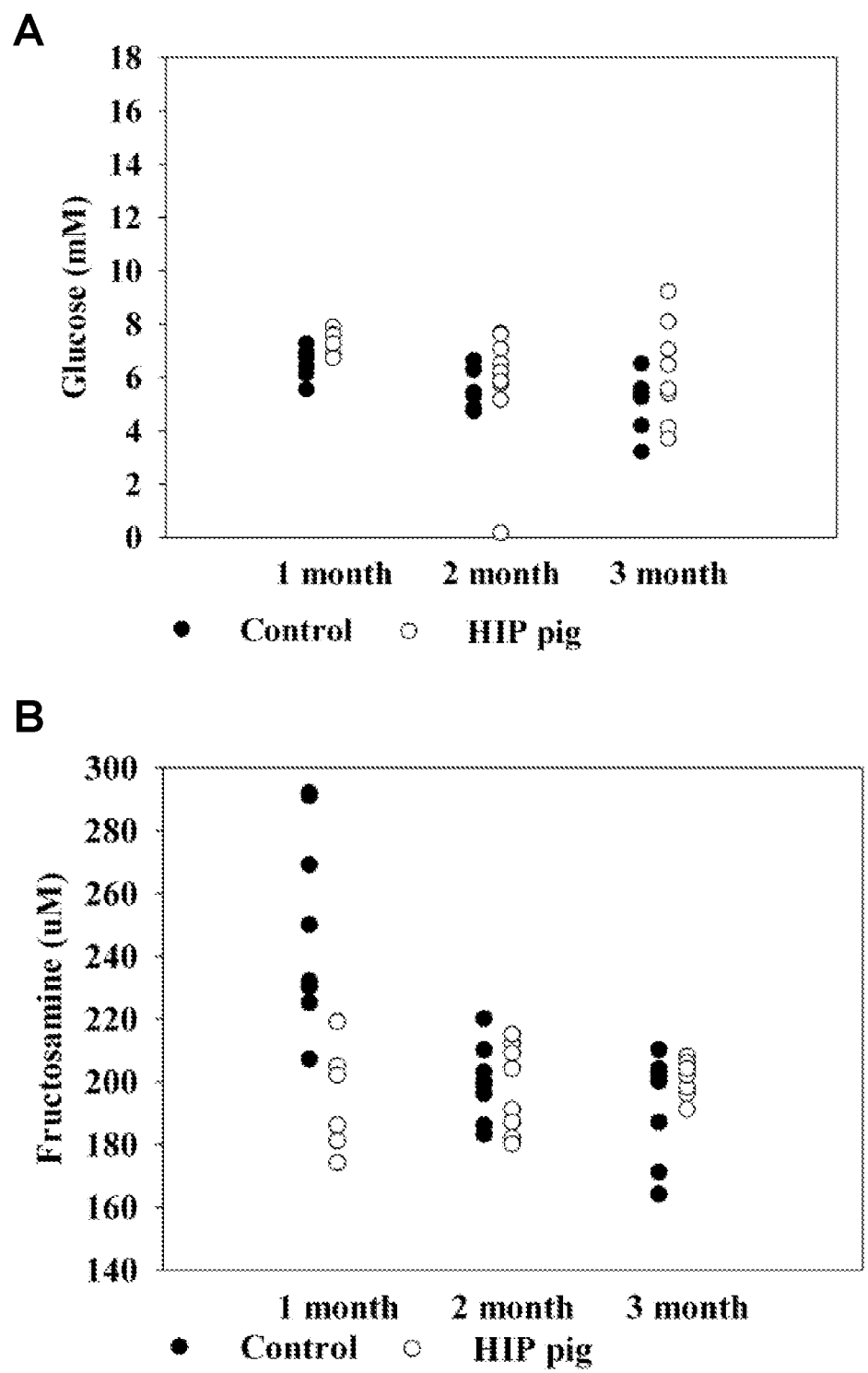
FIG. 5. Characterization of the HIP pigs. Plasmas samples were collected from 8-9 HIP pigs and 8 wild type control pigs without a mutated IAPP gene at age 1, 2, and 3 months. Levels of glucose, fructosamine (FRA), glucagon, insulin and c-peptide were determined. (A) The average glucose level is increased in HIP pigs at age 1, 2, and 3 months when compared to control pigs. (B) The average fructosamine level is increased in HIP pigs at 3 months when compared to control pigs. (C) The average glucagon level is increased in HIP pigs when compares to control pigs. (D) The average insulin level is decreased in HIP pigs when compares to control pigs. (E) The average c-peptide level is decreased in HIP pigs when compared to control pigs. The average c-peptide level in most of the HIP pigs was too low to be measured from age 2 month. For illustration, these results were plotted below the zero level.
Figure 6:
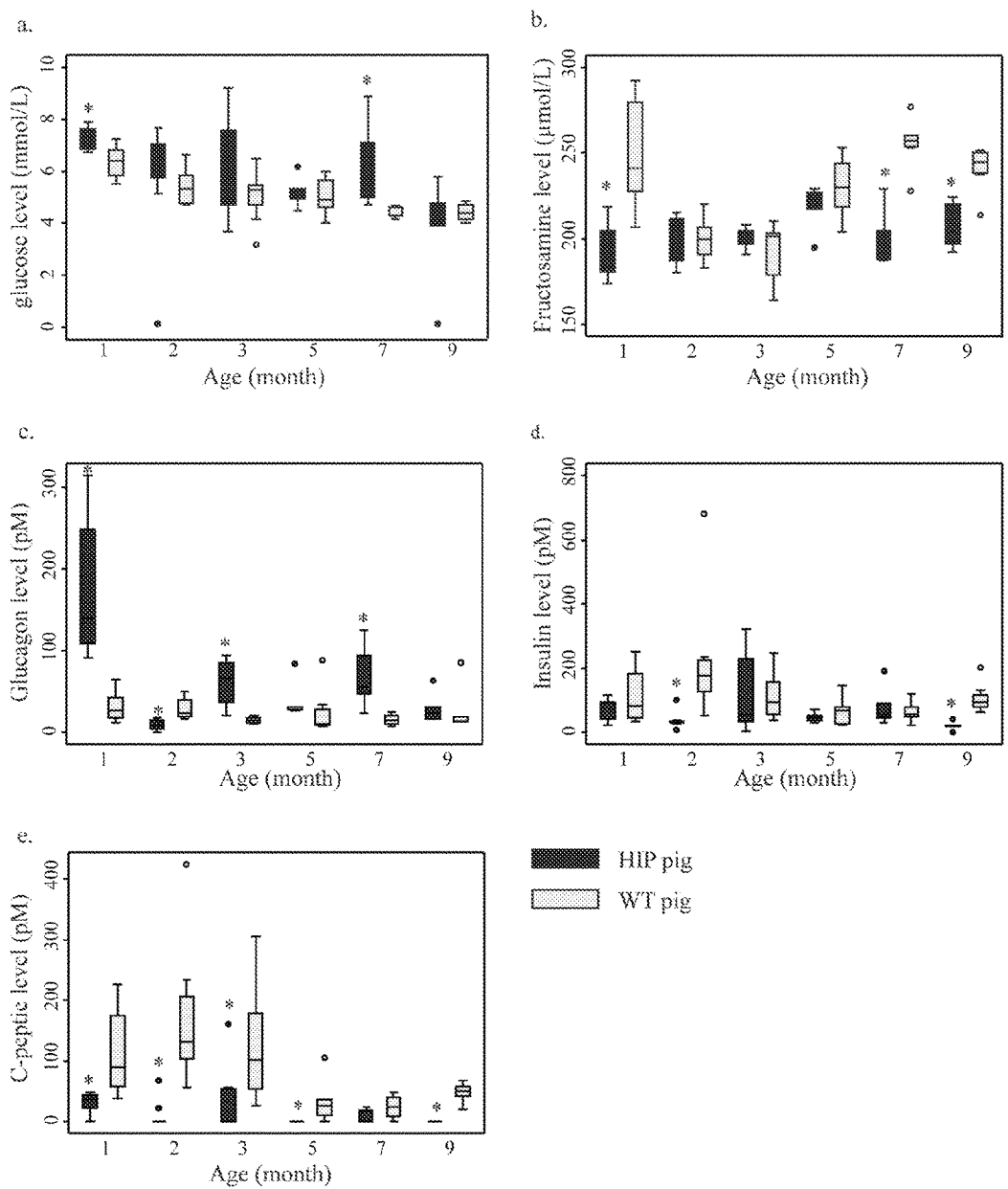
FIG. 6. HIP modification abolishes plasma peptide hormone level. Course of plasma glucose (a), fructosamine (b), glucagon (c), insulin (d), and C-peptide (e) levels from age 1 month to age 9 months. Eight HIP pig (black box) and eight age-match control pigs (white box) were used for the time course study. The eligible HIP pigs for each time point was 7, 8, 8, 6, 5, and 5 for age 1, 2, 3, 5, 7, and 9 months, respectively. Asterisks represent statistically significant ($p<0.05$, ANOVA) between the HIP pig and control at the corresponding time point.

Many abnormal phenotypes, such as blindness, inflammation, infection, and minor organ malformations, have been observed in the HIP pigs. Body weight and whole blood glucose have been monitored in the HIP pigs weekly in the first month, and biweekly thereafter. Some HIP pigs were gaining weight well while others did not thrive. Pigs that were losing weight and showing signs of suffering were euthanized. Blood glucose was monitored in the HIP pigs weekly for the first month and then biweekly. Fluctuating, but high, glucose levels were observed in all HIP pigs. After weaning, the blood glucose in the HIP pigs was getting more normal due the strict diet given every day (FIG. 4). Our data from the first months show that these HIP pigs have significantly higher glucagon and lower c-peptide levels than control pigs, suggesting that the genetic modification we have introduced in the pigs already had effects in the young pigs (FIG. 5). The pigs will be bred as soon as they reach sexual maturity.

Levels of glucose, fructosamine (FRA), glucagon, insulin and c-peptide were determined (FIG. 5). FIG. 5A illustrates that the average glucose level is increased in HIP pigs at age 1, 2, and 3 months when compared to control pigs. FIG. 5A illustrates that the average fructosamine level is increased in HIP pigs at 3 months when compared to control pigs, whereas FIG. 5C demonstrates that the average glucagon level is increased in HIP pigs when compares to control pigs. FIG. 5D demonstrates that average insulin level is decreased in HIP pigs when compared to control pigs, and FIG. 5E shows that average c-peptide level is decreased in HIP pigs when compared to control pigs. The average c-peptide level in most of the HIP pigs was too low to be measured from age 2 month. For illustration, these results were plotted below the zero level (FIG. 5E).

In addition, the nonfasting glucose, fructosamine, glucagon, insulin and C-peptide levels in all F0 compound heterozygous)(IAPP$^{S20G}$/IAPP$^{KO}$) HIP pigs at the age of 1, 2, 3, 5, 7 and 9 months were determined and compared to levels of the corresponding wild type pigs. All pigs were fed with normal diet.

As shown FIG. 1, the glucose level in the HIP pigs was statistically significant higher in the HIP pigs at age 1 and 7 month. The plasma fructosamine level, glycosylated serum proteins, was significantly higher in the control pigs than the HIP pigs at age 1, 7, and 9 months. This might be due the low plasma albumin level in the HIP pigs (data no shown). Glucagon is a hormone that elevates the blood glucose level. A high variable glucagon level was observed in the HIP pigs, with significantly higher level at age 1, 3, and 7 month months than the control pigs. Furthermore, the two peptide hormones, insulin and C-peptide, was measured. These hormones act by lowering the blood glucose level. Low insulin level was found in the HIP pigs at age 2 and 9 months. Most strikingly, we found that the C-peptide level in most of the HIP pigs was too low to be detected, indicating a defect in C-peptide production or secretion in the HIP pigs.

The results demonstrate that the genetic modification of the IAPP gene has affected the normal pancreatic functions in the HIP pigs.

Conclusion

In conclusion, a novel porcine model (HIP pigs) with a strong susceptibility towards diabetes has been generated. The HIP pig is deficient of the endogenous porcine IAPP gene, and comprises the human IAPP gene having the mutation S20G as described elsewhere herein. The data demonstrates that pancreatic dysfunction develops already in very young HIP pigs.

SEQUENCES

Human IAPP nucleotide sequence, encoding a 89 amino acid peptide (22 amino acid signal peptide + 67 amino acid pro-amylin)
SEQ ID NO: 1
ATGGGCATCCTGAAGCTGCAAGTATTTCTCATTGTGCTCTCTGTTGCATT

GAACCATCTGAAAGCTACACCCATTGAAAGTCATCAGGTGGAAAAGCGGA

AATGCAACACTGCCACATGTGCAACGCAGCGCCTGGCAAATTTTTTAGTT

CATTCCaGCAACAACTTTGGTGCCATTCTCTCATCTACCAACGTGGGATC

CAATACATATGGCAAGAGGAATGCAGTAGAGGTTTTAAAGAGAGAGCCAC

TGAATTACTTGCCCCTTTAG

Human IAPP nucleotide sequence, encoding 67 amino acid pro-amylin.
SEQ ID NO: 2
ACACCCATTGAAAGTCATCAGGTGGAAAAGCGGAAATGCAACACTGCCAC ATGTGCAACGCAGCGCCTGGCAAATTTTTTAGTTCATTCCaGCAACAACT

TTGGTGCCATTCTCTCATCTACCAACGTGGGATCCAATACATATGGCAAG

AGGAATGCAGTAGAGGTTTTAAAGAGAGAGCCACTGAATTACTTGCCCCT

TTAG

Human IAPP nucleotide sequence encoding the 37 amino acid amylin peptide.
SEQ ID NO: 3
AAATGCAACACTGCCACATGTGCAACGCAGCGCCTGGCAAATTTTTTAGT
TCATTCCaGCAACAACTTTGGTGCCATTCTCTCATCTACCAACGTGGGAT
CCAATACATAT Human IAPP nucleotide sequence, encoding a 89
amino acid peptide (22 amino acid signal peptide +
67 amino acid pro-amylin) and comprising an A157G
mutation (underlined and in bold).
SEQ ID NO: 4
ATGGGCATCCTGAAGCTGCAAGTATTTCTCATTGTGCTCTCTGTTGCATT

GAACCATCTGAAAGCTACACCCATTGAAAGTCATCAGGTGGAAAAGCGGA

AATGCAACACTGCCACATGTGCAACGCAGCGCCTGGCAAATTTTTTAGTT

CATTCCgGCAACAACTTTGGTGCCATTCTCTCATCTACCAACGTGGGATC

CAATACATATGGCAAGAGGAATGCAGTAGAGGTTTTAAAGAGAGAGCCAC

TGAATTACTTGCCCCTTTAG

Human IAPP nucleotide sequence, encoding 67 amino
acid pro-amylin and comprising an A91G mutation
(underlined and in bold).
SEQ ID NO: 5
ACACCCATTGAAAGTCATCAGGTGGAAAAGCGGAAATGCAACACTGCCAC ATGTGCAACGCAGCGCCTGGCAAATTTTTTAGTTCATTCCgGCAACAACT

TTGGTGCCATTCTCTCATCTACCAACGTGGGATCCAATACATATGGCAAG

AGGAATGCAGTAGAGGTTTTAAAGAGAGAGCCACTGAATTACTTGCCCCT

TTAG

Human IAPP nucleotide sequence encoding the 37
amino acid amylin peptide and comprising an A58G
mutation (underlined and in bold)..
SEQ ID NO: 6
AAATGCAACACTGCCACATGTGCAACGCAGCGCCTGGCAAATTTTTTAGT
TCATTCCgGCAACAACTTTGGTGCCATTCTCTCATCTACCAACGTGGGAT
CCAATACATAT Human IAPP amino acid sequence (22 amino acid
signal peptide + 67 amino acid pro-amylin)
SEQ ID NO: 7
GILKLQVFLIVLSVALNHLKATPIESHQVEKRKCNTATCATQRLANFLVH
SSNNFGAILSSTNVGSNTYGKRNAVEVLKREPLNYLPL Human proamylin amino acid sequence
SEQ ID NO: 8
PIESHQVEKRKCNTATCATQRLANFLVHSSNNFGAILSSTNVGSNTYGKR
NAVEVLKREPLNYLPL Human amylin amino acid sequence
SEQ ID NO: 9
KCNTATCATQRLANFLVHSSNNFGAILSSTNVGSNTY Human IAPP amino acid sequence (22 amino acid
signal peptide + 67 amino acid pro-amylin)
comprising the mutation 520G (indicated in bold)
SEQ ID NO: 10
GILKLQVFLIVLSVALNHLKATPIESHQVEKRKCNTATCATQRLANFLVH
SGNNFGAILSSTNVGSNTYGKRNAVEVLKREPLNYLPL Human proamylin amino acid sequence comprising the
mutation S20G (indicated in bold)
SEQ ID NO: 11
PIESHQVEKRKCNTATCATQRLANFLVHSGNNFGAILSSTNVGSNTYGKR
NAVEVLKREPLNYLPL Human amylin amino acid sequence comprising the
mutation S20G (indicated in bold)
SEQ ID NO: 12
KCNTATCATQRLANFLVHSGNNFGAILSSTNVGSNTY Nucleotide sequence of the HIP pig targeting
construct comprising the human mutated IAPP gene
having an 520G mutation. hIAPP sequence are shown
in bold and the 520G mutation are underlined.
SEQ ID NO: 13
CCTGCAGGCAGCTGCGCGCTCGCTCGCTCACTGAGGCCGCCCGGCAAAG

CCCGGGCGTCGGGCGACCTTTGGTCGCCCGGCCTCAGTGAGCGAGCGAGC

GCGCAGAGAGGGAGTGGCCAACTCCATCACTAGGGGTTCCTGCGGCCGCT

CTGTACAGGACAAGATATGAGAGTATATACCATAAGGTTTCACATGAATT

CTTAAAATACTTACTCTTAGCAAAGACACAGATAATGAAGTACTCCCCAT

ACAAAATAAATACATTGAGATAAAATCTACTGCATTTTGCCTCAAATTAC

ATATATCCACTGGCATCTGGACGTTGAATGAAGCTTCATACCTCTTGTCC

ACTTTATAATTAACCTAAATTTAACTAATATTTTGGTTCCTGTAGAGCTG

AAAATGAAAACATTTCTCTAGAGTTCCTAATAATCCGCAAAAGGCAATGT

TATAATTCTGTATCAATTTCCAGGGCTATTGTGAGAGCGCACTGAAACAA

AAGGTCATACAAACATACGGAATTAACATAAATAAATTAACGCAAATAAA

TTCTGAGATGTTACAATTGAAATGAATTATTTAACCTGGTTATCACTTCT

GACTTATCCATAATATTTCTATGCAGTTATTCCGGGTGGCTGCGTAATAT

GGTGACTATTAATACCATTGACATAAAAAGCCTTTTGGTTTTAACACCTA

ACCCAATCCTATCAGTAAAACTGCTGAAAGCATAGGAACCAAGCAGGGGT

ATAAGAACATGGTAATCTTCATGTATTTATGCTAAGAGTAATAGAATTCC

CACCCTACAATAGTCAGAGTACCTGAACAGGAATTTGATTCCCTTGAGAA

TTTATAATATCTGACATTTCTCTTAACACTCTTGATTCAAGATCTCCAAG

AACTTAACAGAAATTAACATTGGTCATTCTGTGTGAAATGTGTAGGAAGT

GAATATCTATTTTTTTAATTCAGCAAGTTCCAGGTTACTTATTAGTTTAC

ATTCTAAATCCTTTTTTAAAAAAATTGGGAAATAGATTCACAAATATTTT

AAAAAATAGAAGACAAAGATATTTTTAATTATTATTTTCTGGAATATATT

CTGAATTTCCAAAGAAAGGATTGTACTGGGAAATTCAACAAGTGAATTCG

AGCTCGGTACCCGGGGATCCCCCAACCACTCCAAGTGGAGGCTGAGAAAG

GTTTTGTAGCTGGGTAGAGTATGTACTAAGAGATGGAGACAGCTGGCTCT

GAGCTCTGAAGCAAGCACCTCTTATGGAGAGTTGCTGACCTTCAGGTGCA

AATCTAAGATACTACAGGAGAATACACCATGGGGCTTCAGCCCAGTTGAC

TCCCGAGTGGGCTATGGGTTTGTGGAAGGAGAGATAGAAGAGAAGGGACC

TTTCTTCTTGAATTCTGCTTTCCTTCTACCTCTGAGGGTGAGCTGGGGTC

TCAGCTGAGGTGAGGACACAGCTATCAGTGGGAACTGTGAAACAACAGTT

CAAGGGACAAAGTTACTAGGTCCCCCAACAACTGCAGCCTCCTGGGGAAT

GATGTGGAAAAATGCTCAGCCAAGGACAAAGAAGGCCTCACCCTCTCTGA

GACAATGTCCCCTGCTGTGAACTGGTTCATCAGGCCACCCAGGAGCCCCT

ATTAAGACTCTAATTACCCTAAGGCTAAGTAGAGGTGTTGTTGTCCAATG

AGCACTTTCTGCAGACCTAGCACCAGGCAAGTGTTTGGAAACTGCAGCTT

CAGCCCCTCTGGCCATCTGCTGATCCACCCTTAATGGGACAAACAGCAAA

GTCCAGGGGTCAGGGGGGGGGTGCTTTGGACTATAAAGCTAGTGGGATT

CAGTAACCCCCTCTAAAGCTTGATGGGGCTGAGAACTTCAGGGTGAGTTT

GGGGACCCTTGATTGTTCTTTCTTTTTCGCTATTGTAAAATTCATGTTAT

ATGGAGGGGGCAAAGTTTTCAGGGTGTTGTTTAGAATGGGAAGATGTCCC

TTGTATCACCATGGACCCTCATGATAATTTTGTTTCTTTCACTTTCTACT

CTGTTGACAACCATTGTCTCCTCTTATTTTCTTTTCATTTTCTGTAACTT

-continued

TTTCGTTAAACTTTAGCTTGCATTTGTAACGAATTTTTAAATTCACTTTT
GTTTATTTGTCAGATTGTAAGTACTTTCTCTAATCACTTTTTTTTCAAGG
CAATCAGGGTATATTATATTGTACTTCAGCACAGTTTTAGAGAACAATTG
TTATAATTAAATGATAAGGTAGAATATTTCTGCATATAAATTCTGGCTGG
CGTGGAAATATTCTTATTGGTAGAAACAACTACATCCTGGTCATCATCCT
GCCTTTCTCTTTATGGTTACAATGATATACACTGTTTGAGATGAGGATAA
AATACTCTGAGTCCAAACCGGGCCCCTCTGCTAACCATGTTCATGCCTTC
TTCTCTTTCCTACAGCTCCTGGGCAACGTGCTGGTTGTTGTGCTGTCTCA
TCATTTTGGCAAAGAATTCACCATGAAGTTCCTATTCTCTAGAAAGTATA
GGAACTTCGGCATCCTGAAGCTGCAAGTATTTCTCATTGTGCTCTCTGTT
GCATTGAACCATCTGAAAGCTACACCCATTGAAAGTCATCAGGTGGAAAA
GCGGAAATGCAACACTGCCACATGTGCAACGCAGCGCCTGGCAAATTTTT
TAGTTCATTCCgGCAACAACTTTGGTGCCATTCTCTCATCTACCAACGTG
GGATCCAATACATATGGCAAGAGGAATGCAGTAGAGGTTTTAAAGAGAGA
GCCACTGAATTACTTGCCCCTTTAGAAGGGCGAATAACGTGCTAAAGGGA
ACAAAAGCTGGAGCTCCACCGCGGATAACTTCGTATAGCATACATTATAC
GAAGTTATCGCGCCCTACCGGGTAGGGGAGGCGCTTTTCCCAAGGCAGTC
TGGAGCATGCGCTTTAGCAGCCCCGCTGGGCACTTGGCGCTACACAAGTG
GCCTCTGGCCTCGCACACATTCCACATCCACCGGTAGGCGCCAACCGGCT
CCGTTCTTTGGTGGCCCCTTCGCGCCACCTTCTACTCCTCCCCTAGTCAG
GAAGTTCCCCCCGCCCCGCAGCTCGCGTCGTGCAGGACGTGACAAATGG
AAGTAGCACGTCTCACTAGTCTCGTGCAGATGGACAGCACCGCTGAGCAA
TGGAAGCGGGTAGGCCTTTGGGGCAGCGGCCAATAGCAGCTTTGGCTCCT
TCGCTTTCTGGGCTCAGAGGCTGGGAAGGGGTGGGTCCGGGGCGGGCTC
AGGGGCGGGCTCAGGGCGGGGCGGGCGCCCGAAGGTCCTCCGGAAGCCC
GGCATTCTGCACGCTTCAAAAGCGCACGTCTGCCGCGCTGTTCTCCTCTT
CCTCATCTCCGGGCCTTTCGACCTGCAGCCAATATGGGATCGGCCATTGA
ACAAGATGGATTGCACGCAGGTTCTCCGGCCGCTTGGGTGGAGAGGCTAT
TCGGCTATGACTGGGCACAACAGACAATCGGCTGCTCTGATGCCGCCGTG
TTCCGGCTGTCAGCGCAGGGGCGCCCGGTTCTTTTTGTCAAGACCGACCT
GTCCGGTGCCCTGAATGAACTGCAGGACGAGGCAGCGCGGCTATCGTGGC
TGGCCACGACGGGCGTTCCTTGCGCAGCTGTGCTCGACGTTGTCACTGAA
GCGGGAAGGGACTGGCTGCTATTGGGCGAAGTGCCGGGGCAGGATCTCCT
GTCATCTCACCTTGCTCCTGCCGAGAAAGTATCCATCATGGCTGATGCAA
TGCGGCGGCTGCATACGCTTGATCCGGCTACCTGCCCATTCGACCACCAA
GCGAAACATCGCATCGAGCGAGCACGTACTCGGATGGAAGCCGGTCTTGT
CAATCAGGATGATCTGGACGAAGAGCATCAGGGGCTCGCGCCAGCCGAAC
TGTTCGCCAGGCTCAAGGCGCGCATGCCCGACGGCGAGGATCTCGTCGTG
ACCCATGGCGATGCCTGCTTGCCGAATATCATGGTGGAAAATGGCCGCTT
TTCTGGATTCATCGACTGTGGCCGGCTGGGTGTGGCGGATCGCTATCAGG
ACATAGCGTTGGCTACCCGTGATATTGCTGAAGAGCTTGGCGGCGAATGG

-continued

GCTGACCGCTTCCTCGTGCTTTACGGTATCGCCGCTCCCGATTCGCAGCG
CATCGCCTTCTATCGCCTTCTTGACGAGTTCTTCTGAGATATCGTCGACG
ATATCATAACTTCGTATAGCATACATTATACGAAGTTATTGAATTCCTGC
AGCCCGGGGGATCCGCCCCTCTCCCTCCCCCCCCCCTAACGTTACTGGCC
GAAGCCGCTTGGAATAAGGCCGGTGTGCGTTTGTCTATATGTTATTTTCC
ACCATATTGCCGTCTTTTGGCAATGTGAGGGCCCGGAAACCTGGCCCTGT
CTTCTTGACGAGCATTCCTAGGGGTCTTTCCCCTCTCGCCAAAGGAATGC
AAGGTCTGTTGAATGTCGTGAAGGAAGCAGTTCCTCTGGAAGCTTCTTGA
AGACAAACAACGTCTGTAGCGACCCTTTGCAGGCAGCGGAACCCCCCACC
TGGCGACAGGTGCCTCTGCGGCCAAAAGCCACGTGTATAAGATACACCTG
CAAAGGCGGCACAACCCCAGTGCCACGTTGTGAGTTGGATAGTTGTGGAA
AGAGTCAAATGGCTCTCCTCAAGCGTATTCAACAAGGGGCTGAAGGATGC
CCAGAAGGTACCCCATTGTATGGGATCTGATCTGGGGCCTCGGTGCACAT
GCTTTACATGTGTTTAGTCGAGGTTAAAAAAACGTCTAGGCCCCCCGAAC
CACGGGGACGTGGTTTTCCTTTGAAAAACACGATGATAATATGGCCACAG
AAGTTCCTATTCttcaaataGTATAGGAACTTCACCATGGTGCACGTGGA
TCCAAAAAAGAAGAGAAAGGTAGATCCAAAAAAGAAGAGAAAGGTAGATC
CAAAAAAGAAGAGAAAGGTACACGTGTCCATGGTGAGCAAGGGCGAGGAG
CTGTTCACCGGGGTGGTGCCCATCCTGGTCGAGCTGGACGGCGACGTAAA
CGGCCACAAGTTCAGCGTGTCCGGCGAGGGCGAGGGCGATGCCACCTACG
GCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCG
CTACCCCGACCACATGAAGCAGCACGACTTCTTCAAGTCCGCCATGCCCG
AAGGCTACGTCCAGGAGCGCACCATCTTCTTCAAGGACGACGGCAACTAC
AAGACCCGCGCCGAGGTGAAGTTCGAGGGCGACACCCTGGTGAACCGCAT
CGAGCTGAAGGGCATCGACTTCAAGGAGGACGGCAACATCCTGGGGCACA
AGCTGGAGTACAACTACAACAGCCACAACGTCTATATCATGGCCGACAAG
CAGAAGAACGGCATCAAGGTGAACTTCAAGATCCGCCACAACATCGAGGA
CGGCAGCGTGCAGCTCGCCGACCACTACCAGCAGAACACCCCCATCGGCG
ACGGCCCCGTGCTGCTGCCCGACAACCACTACCTGAGCACCCAGTCCGCC
CTGAGCAAAGACCCCAACGAGAAGCGCGATCACATGGTCCTGCTGGAGTT
CGTGACCGCCGCCGGGATCACTCTCGGCATGGACGAGCTGTACAAGTAAA
GGTCAACGCACCTCTAAAGTTCTTATTGCTTTATGTATAAATACCCTAGT
GATTTCCTGTATAATTTAACAGTACCTTTTTCATTTCTAAAGTGAATATG
TGAATCTGTGTGTCCCATGTTTGCTGCCAGTACATGTAAACTGTTGTGCT
GAGAATTGTTTTAAATTTAATACTAATCAAGATCCCTTAATAAAAGGCA
AAGTCTTTACAAATGAAATATTCTTCCTGTAGATTTTTATTTAAAAAAAA
AAAAACATTTTAAAAAGTCATTTATTTTTTCCTGTATATTTATGACCTGA
GTTTTCCAACAAAGGAGGAAATGGTTGTTGGCAACTTGGTAAACTGTAAA
CAGCTAATAGTAAAGTTATGATGCTGAACATTAGAAAATCAGCAATTATT -continued

```
AGTACCCTTGATAAGCAATCTCTTTTGCATTCAATTTATGAAATGAGATA
AAATGTTGTTTAAAAAAAATAAAGACTGCTCCTGACTCAGTCAAAATATT
TTTTAAAACTCTGGTTTTTGTTGTACTTGCTGATACTAAGAGTTTACTTA
AAAATATAAAACCCAATTTGCGTCCATGAGGATTTCACTGTGTTTCATCA
ACAGTGGGCTTTTATTAAATGTATATGCCTTTTATTCTATTTAAGTGGCT
TTCAGCAAATCTTTGTCATATTTTTATACAGAGTGCTGTACCAGCAAGTA
CAACAAAAAAGCAAAAACAACAAACTTTATAATTTGGTAATCTTAAGGCA
TACTTCATAAGGGGAAATTTTTATGTATTTATACATAAATACCCTAGTGA
TTTCCTGTTACTATGAAACTTATTCCAACCAGGAGACTTGAGAAGGAAAG
AAGCTATTACCTTGATAAAATAGGTATTAATAGTAGATATTATTCTAAAG
TTTATTCATTAAAATTATTATCAAAGTGAAACGTGAACAAAATCAGAATT
ATTTCCTCAGTTGATATTCCTAGGCCAGTAGGAATCTAAGTATATGAACC
TTGGGAATACGAGACTGCCATGGAGTGCCCCAAATACTTTCCCTGGTTTC
TCATAATTACCTTGTGAAATAATAATGAGCTTTTCTTTATTGATATAACT
GGAGATAGCAACAGTAAGTTTTGGTGGCTAATTTCATCCCATCTTTTCTC
ATTGTATCTACCATGCTTGAAATCATAGGTACCCTTGGATAATCTTCCAA
ATACTTATGTACATGCTACAAATTATATTTTATTGAAGTTTTAGAAACAC
AAATGATTCTTCTATCTCCCATGTTGCAATACAGAGTCAGGACAAATAAT
TTATTAATTAATACTGTGTTTAAAATTTCTAGGGCCCTTAAAAAAAAAGA
CAAAGGGAGTTCCCATCGTGGCTCAGCAGAAACAAATCAGACTGGCATCC
ATGAGGAAGCAGGTTCCATCCCTGGCTTTGCTCAGTGGGTTCAGGATCTG
GCGTTGCTGTGAGCTGTTGGGTAGATTGCAGACATGGCTCAGATCTGACA
TTGCTGTGGCTGTGGTGTAGGCTGGCGGCTACAGCTCTGATTTGACCCCT
AGTCTGGGAATGGCCATATGCCATGGGTGTCGCCCTTAAAAAAAAGAAA
AGAAAACAACTAGAAATTCTCCTGATCATTGTGAGATGACATTCTGCAAT
AAGCCTCATACTTCGCTGAGGGGTTGAATATCATTACCTCATGAAATATG
CTTAGATAAAGAATACCTTTTGGTTAAGAGTAGAAAAGCCTATGAGTCTA
AAGCTCCTTAGGCTGAGTGCAGAGAGAGCTTTTCATGCAAAGTAGAATAT
TTTCTTTTTCTAACCATTATCCCCTCACCCTCTGGGCATTTACACCCAGG
TTCTACTCAAATGCCACATTCTGCAAGGAACTTGTCTGAACTTACATAGA
TTTTTATCTATATTTTCTGACACCAGTTTATTCAGACATGCGGCCGCAGG
AACCCCTAGTGATGGAGTTGGCCACTCCCTCTCTGCGCGCTCGCTCGCTC
ACTGAGGCCGGGCGACCAAAGGTCGCCCGACGCCCGGGCTTTGCCCGGGC
GGCCTCAGTGAGCGAGCGAGCGCGCAGCTGCCTGCAGGGGCGCCTGATGC
GGTATTTTCTCCTTACGCATCTGTGCGGTATTTCACACCGCATACGTCAA
AGCAACCATAGTACGCGCCCTGTAGCGGCGCATTAAGCGCGGCGGGTGTG
GTGGTTACGCGCAGCGTGACCGCTACACTTGCCAGCGCCCTAGCGCCCGC
TCCTTTCGCTTTCTTCCCTTCCTTTCTCGCCACGTTCGCCGGCTTTCCCC
GTCAAGCTCTAAATCGGGGGCTCCCTTTAGGGTTCCGATTTAGTGCTTTA
CGGCACCTCGACCCCAAAAAACTTGATTTGGGTGATGGTTCACGTAGTGG
GCCATCGCCCTGATAGACGGTTTTTCGCCCTTTGACGTTGGAGTCCACGT
TCTTTAATAGTGGACTCTTGTTCCAAACTGGAACAACACTCAACCCTATC
TCGGGCTATTCTTTTGATTTATAAGGGATTTTGCCGATTTCGGCCTATTG
GTTAAAAAATGAGCTGATTTAACAAAAATTTAACGCGAATTTTAACAAAA
TATTAACGTTTACAATTTTATGGTGCACTCTCAGTACAATCTGCTCTGAT
GCCGCATAGTTAAGCCAGCCCCGACACCCGCCAACACCCGCTGACGCGCC
CTGACGGGCTTGTCTGCTCCCGGCATCCGCTTACAGACAAGCTGTGACCG
TCTCCGGGAGCTGCATGTGTCAGAGGTTTTCACCGTCATCACCGAAACGC
GCGAGACGAAAGGGCCTCGTGATACGCCTATTTTTATAGGTTAATGTCAT
GATAATAATGGTTTCTTAGACGTCAGGTGGCACTTTTCGGGGAAATGTGC
GCGGAACCCCTATTTGTTTATTTTTCTAAATACATTCAAATATGTATCCG
CTCATGAGACAATAACCCTGATAAATGCTTCAATAATATTGAAAAGGAA
GAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAA
GATGCTGAAGATCAGTTGGGTGCACGAGTGGGTTACATCGAACTGGATCT
CAACAGCGGTAAGATCCTTGAGAGTTTTCGCCCCGAAGAACGTTTTCCAA
TGATGAGCACTTTTAAAGTTCTGCTATGTGGCGCGGTATTATCCCGTATT
GACGCCGGGCAAGAGCAACTCGGTCGCCGCATACACTATTCTCAGAATGA
CTTGGTTGAGTACTCACCAGTCACAGAAAAGCATCTTACGGATGGCATGA
CAGTAAGAGAATTATGCAGTGCTGCCATAACCATGAGTGATAACACTGCG
GCCAACTTACTTCTGACAACGATCGGAGGACCGAAGGAGCTAACCGCTTT
TTTGCACAACATGGGGGATCATGTAACTCGCCTTGATCGTTGGGAACCGG
AGCTGAATGAAGCCATACCAAACGACGAGCGTGACACCACGATGCCTGTA
GCAATGGCAACAACGTTGCGCAAACTATTAACTGGCGAACTACTTACTCT
AGCTTCCCGGCAACAATTAATAGACTGGATGGAGGCGGATAAAGTTGCAG
GACCACTTCTGCGCTCGGCCCTTCCGGCTGGCTGGTTTATTGCTGATAAA
TCTGGAGCCGGTGAGCGTGGGTCTCGCGGTATCATTGCAGCACTGGGGCC
AGATGGTAAGCCCTCCCGTATCGTAGTTATCTACACGACGGGGAGTCAGG
CAACTATGGATGAACGAAATAGACAGATCGCTGAGATAGGTGCCTCACTG
ATTAAGCATTGGTAACTGTCAGACCAAGTTTACTCATATATACTTTAGAT
TGATTTAAAACTTCATTTTTAATTTAAAAGGATCTAGGTGAAGATCCTTT
TTGATAATCTCATGACCAAAATCCCTTAACGTGAGTTTTCGTTCCACTGA
GCGTCAGACCCCGTAGAAAAGATCAAAGGATCTTCTTGAGATCCTTTTTT
TCTGCGCGTAATCTGCTGCTTGCAAACAAAAAAACCACCGCTACCAGCGG
TGGTTTGTTTGCCGGATCAAGAGCTACCAACTCTTTTTCCGAAGGTAACT
GGCTTCAGCAGAGCGCAGATACCAAATACTGTCCTTCTAGTGTAGCCGTA
GTTAGGCCACCACTTCAAGAACTCTGTAGCACCGCCTACATACCTCGCTC
TGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGG
CTGAACGGGGGGTTCGTGCACACAGCCCAGCTTGGAGCGAACGACCTACA
CCGAACTGAGATACCTACAGCGTGAGCTATGAGAAAGCGCCACGCTTCCC
```

-continued
GAAGGGAGAAAGGCGGACAGGTATCCGGTAAGCGGCAGGGTCGGAACAGG

AGAGCGCACGAGGGAGCTTCCAGGGGGAAACGCCTGGTATCTTTATAGTC

CTGTCGGGTTTCGCCACCTCTGACTTGAGCGTCGATTTTTGTGATGCTCG

-continued
TCAGGGGGCGGAGCCTATGGAAAAACGCCAGCAACGCGGCCTTTTTACG

GTTCCTGGCCTTTTGCTGGCCTTTTGCTCACATGT

The invention claimed is:

1. A transgenic pig comprising in its genome a mutated human Islet Amyloid Polypeptide (hIAPP) gene operably linked to a rat insulin promoter wherein said mutated hIAPP gene comprises a mutation resulting in the amino acid substitution S20G of active amylin, as reflected in SEQ ID NO:12 and is inserted into exon 2 of the endogenous IAPP gene of the porcine genome wherein said insertion results in reduction or ablation of the expression of the endogenous IAPP gene and wherein said pig displays at least one phenotype associated with diabetes selected from the group consisting of higher glucose levels, higher glucagon levels, lower insulin levels, and/or lower c-peptide levels when compared to a control pig.

2. The transgenic pig according to claim 1, wherein said transgenic pig does not express an endogenous pig IAPP gene.

3. The transgenic pig according to claim 2, wherein said endogenous pig IAPP gene has been knocked out.

4. The transgenic pig according to claim 1, wherein said transgenic pig is a mini-pig.

5. The transgenic pig according to claim 1 wherein said glucose level and/or said glucagon level is increased by at least 10% when compared to a control pig and wherein said transgenic pig and said control pig are given a normal diet.

6. The transgenic pig according to claim 1, wherein said insulin level and/or said c-peptide level is decreased by at least 10% when compared to a control pig when said transgenic pig and said control pig are given a normal diet.

7. The transgenic pig according to claim 5, wherein said control pig does not comprise a mutated IAPP gene.

8. The transgenic pig according to claim 1, wherein said transgenic pig displays hyperglycemia.

9. The transgenic pig according to claim 1, wherein said transgenic pig displays β-cell degradation.

10. The transgenic pig according to claim 1, wherein said transgenic pig displays at least one phenotype selected from the group consisting of blindness, inflammation, infection, and organ deformation.

11. A transgenic blastocyst, embryo, fetus, donor cell and/or cell nucleus derived from the transgenic pig according to claim 1.

12. A method for producing the transgenic pig according to claim 1, said method comprising:
  i. producing a porcine oocyte having a partially digested zona pellucida,
  ii. separating the oocyte into at least two parts obtaining an oocyte having a nucleus and at least one cytoplast,
  iii. introducing an expression vector encoding the TALEN pair as set forth in TALEN-1 (SEQ ID NO: 14 and SEQ ID NO: 15) or TALEN-2 (SEQ ID NO: 16 and SEQ ID NO: 17) in a donor pig cell and introducing a targeting vector as set forth in SEQ ID NO: 13 into the genome of a donor pig cell resulting in a porcine donor cell comprising in its genome a mutated hIAPP gene operably linked to a rat insulin promoter, inserted into exon 2 of the endogenous IAPP gene of the porcine genome wherein said mutated hIAPP gene comprises a mutation resulting in the amino acid substitution S20G of active amylin, as reflected in SEQ ID NO: 12,
  iv. fusing at least one porcine cytoplast with the donor cell,
  v. obtaining a porcine reconstructed embryo,
  vi. activating the reconstructed embryo to form an embryo, culturing said embryo, and
  vii. transferring said cultured embryo to a porcine host, wherein the embryo develops into a transgenic pig.

13. The method according to claim 12, wherein said donor cell does not express an endogenous pig IAPP gene.

14. The method according to claim 13, wherein said endogenous pig IAPP gene has been knocked out.

15. A method for studying therapy, treatment and/or prevention of diabetes comprising the steps of
  i. providing a transgenic pig according to claim 1
  ii. providing a compound to be tested,
  iii. administering said compound to said transgenic pig,
  iv. determining one or more risk factors of said transgenic pig associated with diabetes, the one or more risk factors selected from the group consisting of insulin level, glucose level, glucagon level and/or c-peptide level,
thereby determining the effect of said compound on the insulin level, glucose level, glucagon level and/or c-peptide level of said transgenic pig.

16. The transgenic pig according to claim 1, wherein said mutated hIAPP gene is inserted using a targeting vector.

\* \* \* \* \*